(12) United States Patent
Hiorth et al.

(10) Patent No.: US 10,945,718 B2
(45) Date of Patent: Mar. 16, 2021

(54) DEVICE FOR HEART REPAIR

(71) Applicant: CARDIOMECH AS, Trondheim (NO)

(72) Inventors: Nikolai Hiorth, Oslo (NO); Jacob Bergsland, Oslo (NO)

(73) Assignee: CARDIOMECH AS, Trondheim (NO)

(*) Notice: Subject to any disclaimer, the term of this patent is extended or adjusted under 35 U.S.C. 154(b) by 398 days.

(21) Appl. No.: 15/511,365

(22) PCT Filed: Sep. 16, 2015

(86) PCT No.: PCT/EP2015/071207
§ 371 (c)(1),
(2) Date: Mar. 15, 2017

(87) PCT Pub. No.: WO2016/042022
PCT Pub. Date: Mar. 24, 2016

(65) Prior Publication Data
US 2017/0252032 A1  Sep. 7, 2017

(30) Foreign Application Priority Data
Sep. 17, 2014  (GB) .................................. 1416383.6

(51) Int. Cl.
*A61B 17/04* (2006.01)
*A61F 2/24* (2006.01)
*A61B 17/00* (2006.01)

(52) U.S. Cl.
CPC ........ *A61B 17/0401* (2013.01); *A61F 2/2457* (2013.01); *A61F 2/2466* (2013.01);
(Continued)

(58) Field of Classification Search
CPC ...... A61B 17/0401; A61B 2017/00526; A61B 2017/0416; A61B 2017/0427;
(Continued)

(56) References Cited

U.S. PATENT DOCUMENTS 5,330,442 A * 7/1994 Green ................ A61B 17/0487
606/151
6,099,553 A * 8/2000 Hart .................... A61B 17/0487
24/115 A
(Continued)

FOREIGN PATENT DOCUMENTS

AU    2012261998    3/2017
CA    2920384       2/2015
(Continued)

OTHER PUBLICATIONS

Search Report under Section 17(5) for United Kingdom Patent Application No. GB1416383.6, dated Mar. 19, 2015, 4 pages.
(Continued)

*Primary Examiner* — Alexander J Orkin
(74) *Attorney, Agent, or Firm* — Norton Rose Fulbright

(57) ABSTRACT

A catheter device for repair of the heart by implanting an artificial chord is disclosed. The device comprises a leaflet anchor 10 for placement in a leaflet 12 of a heart valve, wherein the leaflet anchor 10 is arranged to be coupled to the artificial chord 14; and a mechanical gripper device 6 for grasping the leaflet 12 of the heart valve, wherein the gripper device 6 comprises a leaflet anchor channel for housing the leaflet anchor 10 in a folded configuration; the gripper device 6 and leaflet anchor 10 being arranged such that when, in use, the gripper device 6 grasps the leaflet 12, the leaflet anchor 10 can be pushed out of the leaflet anchor channel to pierce the leaflet 12 and form the leaflet anchor 10 into an unfolded configuration so that hooked formations of the leaflet anchor 10 can, in use, secure the leaflet anchor 10 in the leaflet 12.

20 Claims, 20 Drawing Sheets

(52) U.S. Cl.
CPC .............. *A61B 2017/00526* (2013.01); *A61B 2017/042* (2013.01); *A61B 2017/0409* (2013.01); *A61B 2017/0414* (2013.01); *A61B 2017/0427* (2013.01); *A61B 2017/0454* (2013.01); *A61B 2017/0464* (2013.01)

(58) Field of Classification Search
CPC .... A61B 2017/0437; A61B 2017/0454; A61B 2017/0496; A61B 2017/0451; A61F 2/2457
See application file for complete search history.

(56) References Cited

U.S. PATENT DOCUMENTS

| | | | |
|---|---|---|---|
| 6,231,561 B1* | 5/2001 | Frazier | A61B 17/00234 604/500 |
| 6,743,239 B1 | 6/2004 | Kuehn et al. | |
| 7,316,706 B2 | 1/2008 | Bloom et al. | |
| 7,632,308 B2 | 12/2009 | Loulmet | |
| 7,635,386 B1 | 12/2009 | Gammie | |
| 7,740,638 B2 | 6/2010 | Hyde | |
| 7,992,567 B2 | 8/2011 | Hirotsuka et al. | |
| 8,096,985 B2 | 1/2012 | Legaspi et al. | |
| 8,186,355 B2 | 5/2012 | Van der Burg et al. | |
| 8,292,884 B2 | 10/2012 | Levine et al. | |
| 8,333,204 B2 | 12/2012 | Saadat | |
| 8,500,800 B2 | 8/2013 | Maisano et al. | |
| 8,545,551 B2 | 10/2013 | Loulmet | |
| 8,690,939 B2 | 4/2014 | Miller et al. | |
| D708,744 S | 7/2014 | Morris et al. | |
| 8,778,016 B2 | 7/2014 | Janovsky et al. | |
| 8,784,439 B1 | 7/2014 | Ward et al. | |
| 8,790,394 B2 | 7/2014 | Miller et al. | |
| 8,900,295 B2 | 12/2014 | Migliazza et al. | |
| 9,039,759 B2 | 5/2015 | Alkhatib et al. | |
| 9,131,928 B2 | 9/2015 | Zlotnick et al. | |
| 9,138,316 B2 | 9/2015 | Bielefeld | |
| 9,204,964 B2 | 12/2015 | Dahlgren et al. | |
| 9,204,965 B2 | 12/2015 | Longoria | |
| 9,226,825 B2 | 1/2016 | Starksen et al. | |
| 9,248,018 B2 | 2/2016 | Chawla | |
| 9,301,842 B2 | 4/2016 | Bielefeld | |
| 9,452,048 B2 | 9/2016 | O'Beirne et al. | |
| 9,474,605 B2 | 10/2016 | Rowe et al. | |
| 9,486,315 B2 | 11/2016 | Chawla | |
| 9,545,309 B2 | 1/2017 | Alkhatib et al. | |
| 9,572,667 B2 | 2/2017 | Solem | |
| 9,622,861 B2 | 4/2017 | Miller et al. | |
| 9,668,860 B2 | 6/2017 | Kudlik et al. | |
| 9,700,412 B2 | 7/2017 | Yaron et al. | |
| 9,730,793 B2 | 8/2017 | Reich et al. | |
| 9,744,038 B2 | 8/2017 | Dahlgren et al. | |
| 9,795,482 B2 | 10/2017 | Duffy et al. | |
| 9,877,833 B1 | 1/2018 | Bishop et al. | |
| 10,159,571 B2 | 12/2018 | De Canniere et al. | |
| 10,213,303 B2 | 2/2019 | Medema et al. | |
| 10,226,339 B2 | 3/2019 | Spence et al. | |
| 10,271,947 B2 | 4/2019 | Alkhatib | |
| 10,285,686 B2 | 5/2019 | Gammie et al. | |
| 10,376,673 B2 | 8/2019 | Van Hoven et al. | |
| 10,405,979 B2 | 9/2019 | Schaffner et al. | |
| 10,433,831 B2 | 10/2019 | Sauer | |
| 2002/0183787 A1 | 12/2002 | Wahr et al. | |
| 2003/0078465 A1* | 4/2003 | Pai | A61B 17/00234 600/16 |
| 2003/0145865 A1 | 8/2003 | Sterman et al. | |
| 2004/0078054 A1* | 4/2004 | Biggs | A61B 17/00234 606/232 |
| 2004/0102809 A1* | 5/2004 | Anderson | A61B 17/0487 606/232 |
| 2004/0186566 A1* | 9/2004 | Hindrichs | A61B 17/00234 623/2.37 |
| 2004/0260317 A1* | 12/2004 | Bloom | A61F 2/2487 606/151 |
| 2004/0260344 A1* | 12/2004 | Lyons | A61B 17/0487 606/232 |
| 2005/0228413 A1* | 10/2005 | Binmoeller | A61B 1/00147 606/153 |
| 2005/0251208 A1 | 11/2005 | Elmer et al. | |
| 2006/0089711 A1* | 4/2006 | Dolan | A61B 17/00234 623/2.37 |
| 2006/0207607 A1 | 9/2006 | Hirotsuka et al. | |
| 2006/0287716 A1 | 12/2006 | Banbury et al. | |
| 2006/0293698 A1 | 12/2006 | Douk | |
| 2006/0293710 A1 | 12/2006 | Foerster et al. | |
| 2007/0049952 A1 | 3/2007 | Weiss | |
| 2007/0049970 A1* | 3/2007 | Belef | A61B 17/0057 606/232 |
| 2007/0083235 A1* | 4/2007 | Jervis | A61B 17/0401 606/232 |
| 2007/0118151 A1 | 5/2007 | Davidson | |
| 2007/0144539 A1* | 6/2007 | van der Burg | A61B 17/0401 128/897 |
| 2007/0270943 A1* | 11/2007 | Solem | A61B 17/0401 623/2.11 |
| 2008/0188873 A1 | 8/2008 | Speziali | |
| 2008/0195126 A1 | 8/2008 | Solem | |
| 2008/0228223 A1 | 9/2008 | Alkhatib | |
| 2008/0243150 A1 | 10/2008 | Starksen et al. | |
| 2009/0287304 A1 | 11/2009 | Dahlgren et al. | |
| 2010/0016958 A1 | 1/2010 | St. Goar et al. | |
| 2010/0042147 A1 | 2/2010 | Janovsky et al. | |
| 2010/0145362 A1 | 6/2010 | McLawhorn et al. | |
| 2010/0161042 A1 | 6/2010 | Maisano et al. | |
| 2010/0217283 A1 | 8/2010 | St. Goar et al. | |
| 2011/0011917 A1 | 1/2011 | Loulmet | |
| 2011/0087067 A1* | 4/2011 | Rodrigues, Jr. | A61B 17/0401 600/37 |
| 2012/0035713 A1 | 2/2012 | Lutter et al. | |
| 2012/0083806 A1 | 4/2012 | Goertzen | |
| 2012/0165930 A1 | 6/2012 | Gifford et al. | |
| 2012/0296373 A1 | 11/2012 | Roorda et al. | |
| 2013/0035757 A1 | 2/2013 | Zentgraf et al. | |
| 2013/0096672 A1 | 4/2013 | Reich et al. | |
| 2013/0172978 A1 | 7/2013 | Vidlund et al. | |
| 2013/0190861 A1 | 7/2013 | Chau et al. | |
| 2013/0253639 A1 | 9/2013 | Alkhatib | |
| 2013/0261663 A1* | 10/2013 | Bittenson | A61B 17/0401 606/232 |
| 2014/0031864 A1 | 1/2014 | Jafari et al. | |
| 2014/0074226 A1 | 3/2014 | Bielefeld et al. | |
| 2014/0088691 A1 | 3/2014 | Bielefeld | |
| 2014/0100604 A1* | 4/2014 | Litvack | A61B 17/0469 606/213 |
| 2014/0142690 A1 | 5/2014 | Kovach et al. | |
| 2014/0207154 A1 | 7/2014 | Bielefeld | |
| 2014/0214152 A1 | 7/2014 | Bielefeld | |
| 2014/0371766 A1 | 12/2014 | Morris et al. | |
| 2015/0032206 A1 | 1/2015 | Alkhatib | |
| 2015/0250590 A1 | 9/2015 | Gries et al. | |
| 2015/0272758 A1 | 10/2015 | Morris et al. | |
| 2015/0313620 A1 | 11/2015 | Suri | |
| 2015/0359531 A1 | 12/2015 | Sauer | |
| 2015/0374492 A1 | 12/2015 | Alkhatib | |
| 2017/0007405 A1 | 1/2017 | Griffin et al. | |
| 2017/0035569 A1 | 2/2017 | Deem et al. | |
| 2017/0049435 A1 | 2/2017 | Sauer et al. | |
| 2017/0156861 A1 | 6/2017 | Longoria et al. | |
| 2017/0258592 A1 | 9/2017 | Longoria | |
| 2017/0304050 A1 | 10/2017 | Keidar et al. | |
| 2018/0014931 A1 | 1/2018 | Morriss et al. | |
| 2018/0289480 A1 | 10/2018 | D'ambra et al. | |
| 2018/0296333 A1 | 10/2018 | Dixon et al. | |
| 2018/0303614 A1 | 10/2018 | Schaffner et al. | |
| 2018/0311037 A1 | 11/2018 | Morriss et al. | |
| 2018/0318083 A1 | 11/2018 | Bolling et al. | |
| 2019/0000614 A1 | 1/2019 | Morriss et al. | |
| 2019/0000624 A1 | 1/2019 | Wilson et al. | |
| 2019/0008639 A1 | 1/2019 | Landon et al. | |
| 2019/0015205 A1 | 1/2019 | Rajagopal et al. | |
| 2019/0029671 A1 | 1/2019 | Zhang et al. | |
| 2019/0029812 A1 | 1/2019 | Gifford et al. | |

(56) References Cited

U.S. PATENT DOCUMENTS

| | | |
|---|---|---|
| 2019/0053903 A1 | 2/2019 | Rohl et al. |
| 2019/0059876 A1 | 2/2019 | Decker et al. |
| 2019/0117400 A1 | 4/2019 | Medema et al. |
| 2019/0167197 A1 | 6/2019 | Abunassar et al. |
| 2019/0175345 A1 | 6/2019 | Schaffner et al. |
| 2019/0175346 A1 | 6/2019 | Schaffner et al. |
| 2019/0183648 A1 | 6/2019 | Trapp et al. |
| 2019/0290260 A1 | 9/2019 | Caffes et al. |
| 2019/0290431 A1 | 9/2019 | Genovese et al. |

FOREIGN PATENT DOCUMENTS

| | | |
|---|---|---|
| CA | 2914495 | 12/2015 |
| CN | 107252327 | 10/1917 |
| CN | 204121085 | 1/2015 |
| CN | 204121092 | 1/2015 |
| CN | 104055600 | 2/2016 |
| CN | 107252327 | 10/2017 |
| CN | 108186163 | 6/2018 |
| CN | 109044564 | 12/2018 |
| CN | 208448390 | 2/2019 |
| CN | 109498216 | 3/2019 |
| DE | 102017002974 | 10/2018 |
| EP | 1330190 | 5/2008 |
| EP | 2537487 | 12/2012 |
| EP | 3027144 | 11/2017 |
| FR | 3063631 | 3/2019 |
| GB | 2530487 | 3/2016 |
| GB | 2563155 | 12/2018 |
| JP | 2018030028 | 3/2018 |
| JP | 2018086571 | 6/2018 |
| JP | 6582748 | 10/2019 |
| WO | WO 8910096 | 11/1989 |
| WO | WO 0003759 | 1/2000 |
| WO | WO 00/60995 | 10/2000 |
| WO | WO 0234167 | 5/2002 |
| WO | WO 03001893 | 1/2003 |
| WO | WO 03/105670 | 12/2003 |
| WO | WO 2004/041119 | 1/2004 |
| WO | WO 2004/017845 | 3/2004 |
| WO | WO 2004/103162 | 12/2004 |
| WO | WO 2004/103434 | 12/2004 |
| WO | WO 2005/110244 | 11/2005 |
| WO | WO 2005/112792 | 12/2005 |
| WO | WO 2006/39199 | 4/2006 |
| WO | WO 2006/039223 | 4/2006 |
| WO | WO 2006/039296 | 4/2006 |
| WO | WO 2006/047709 | 5/2006 |
| WO | WO 2006/116558 | 11/2006 |
| WO | WO 2007/021834 | 2/2007 |
| WO | WO 2007/035449 | 3/2007 |
| WO | WO 2007/056502 | 5/2007 |
| WO | WO 2007/061834 | 5/2007 |
| WO | WO 2007/146338 | 12/2007 |
| WO | WO 2007/146362 | 12/2007 |
| WO | WO 2008/101113 | 8/2008 |
| WO | WO 2010/028502 | 3/2010 |
| WO | WO 2010/098804 | 9/2010 |
| WO | WO 2011/154942 | 12/2011 |
| WO | 2012106328 A1 | 8/2012 |
| WO | WO 2012/102928 | 8/2012 |
| WO | WO 2012/137208 | 10/2012 |
| WO | WO 2013/003613 | 1/2013 |
| WO | WO 2013/082454 | 6/2013 |
| WO | WO 2013/173587 | 11/2013 |
| WO | WO 2013/173618 | 11/2013 |
| WO | WO 2013/175468 | 11/2013 |
| WO | WO 2013/177111 | 11/2013 |
| WO | WO 2013/192107 | 12/2013 |
| WO | WO 2014/011794 | 1/2014 |
| WO | WO 2014/028112 | 2/2014 |
| WO | WO 2014/064695 | 5/2014 |
| WO | WO 2014/093861 | 6/2014 |
| WO | WO 2014/110023 | 7/2014 |
| WO | WO 2014/164151 | 10/2014 |
| WO | WO 2015/061378 | 4/2015 |
| WO | WO 2016/042022 | 3/2016 |
| WO | WO 2019013994 | 1/2019 |
| WO | WO 2019/145941 | 8/2019 |
| WO | WO 2019/154847 | 8/2019 |

OTHER PUBLICATIONS

Search Report under Section 17(6) for United Kingdom Patent Application No. GB1416383.6, dated Dec. 3, 2015, 2 pages.
International Search Report (Form PCT/ISA/210) for International Application No. PCT/EP2015/071207, dated Apr. 19, 2016, 5 pages.
Written Opinion (Form PCT/ISA/237) for International Application No. PCT/EP2015/071207, dated Apr. 19, 2016, 11 pages.
European Search Report Issued in EP Application No. 19157011.8, dated Jun. 3, 2019.
International Search Report and Written Opinion Issued in Corresponding PCT Application No. PCT/EP2015/071207, dated Apr. 19, 2016.
Search Report Under Section 17(5) for United Kingdom Patent Application No. GB1819489.4, dated May 13, 2019.
Search Report Under Section 17(5) for United Kingdom Patent Application No. GB1819484.5, dated May 28, 2019.
Search Report Under Section 17(5) for United Kingdom Patent Application No. GB1819490.2, dated May 16, 2019.
Search Report Under Section 17(5) for United Kingdom Patent Application No. GB1819480.3, dated May 28, 2019.
Search Report Under Section 17(5) for United Kingdom Patent Application No. GB1820258.0, dated May 28, 2019.
Official Communication Issued in Corresponding European Patent Application No. EP 15775117.3, dated Sep. 18, 2019.

* cited by examiner

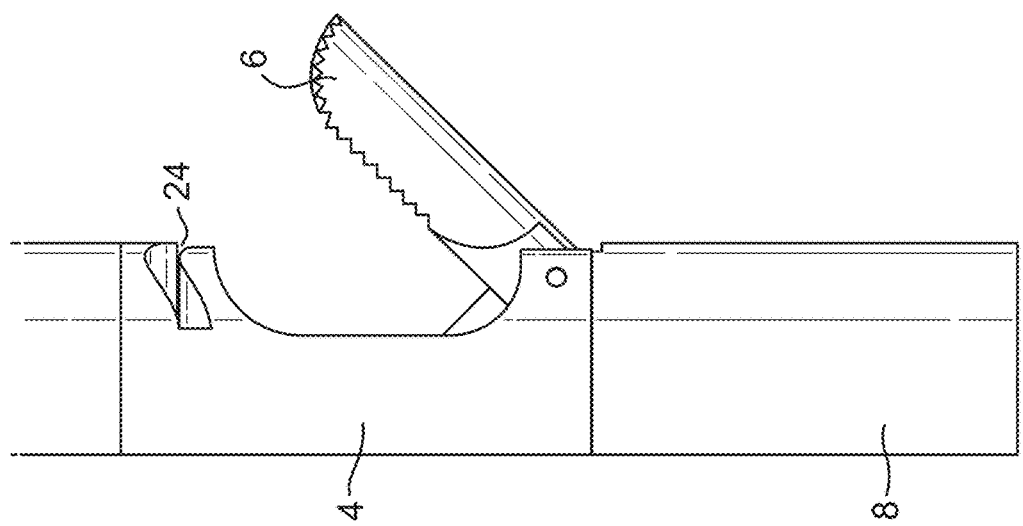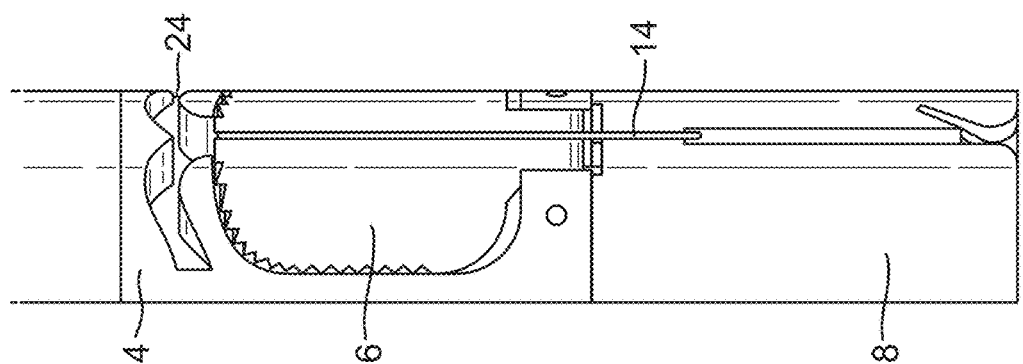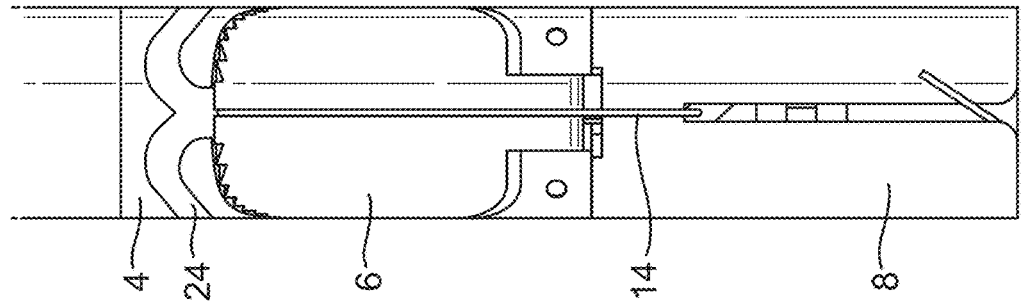

Fig. 33
Fig. 34
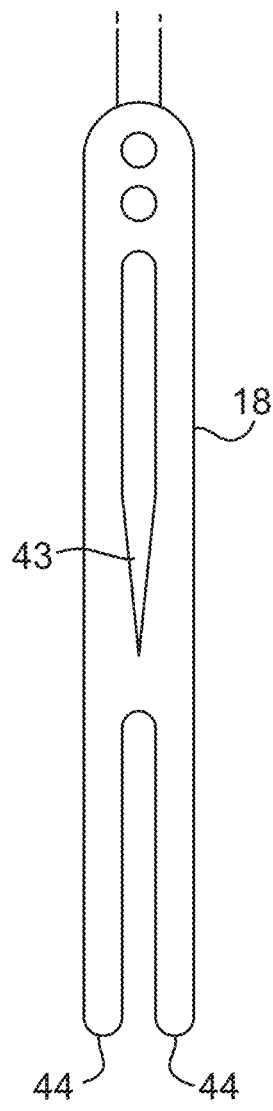
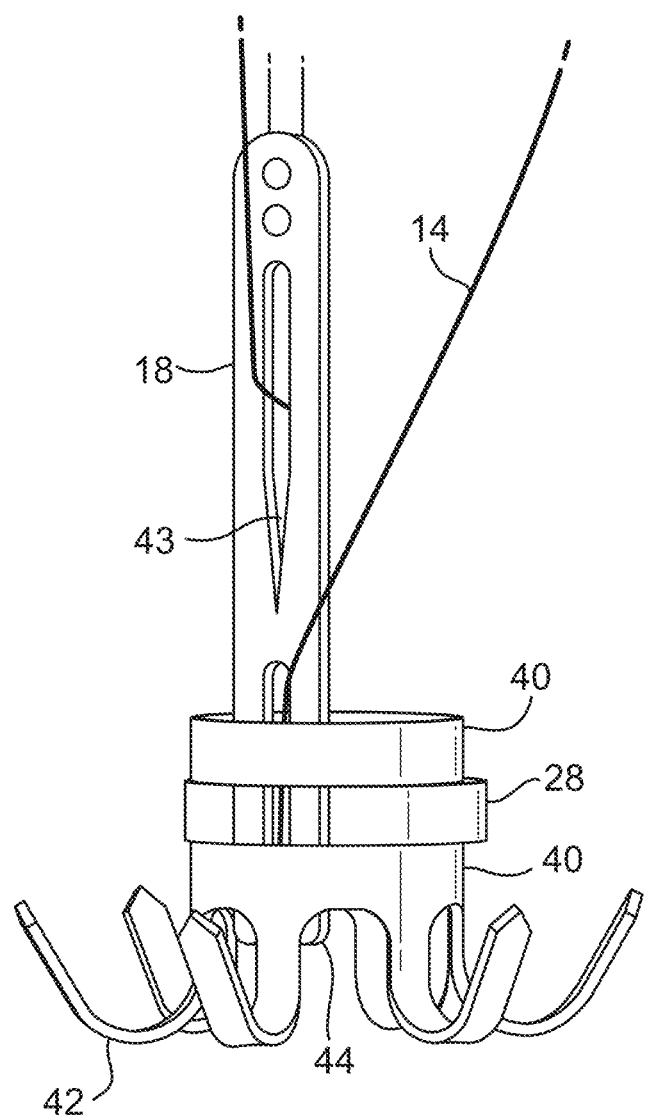

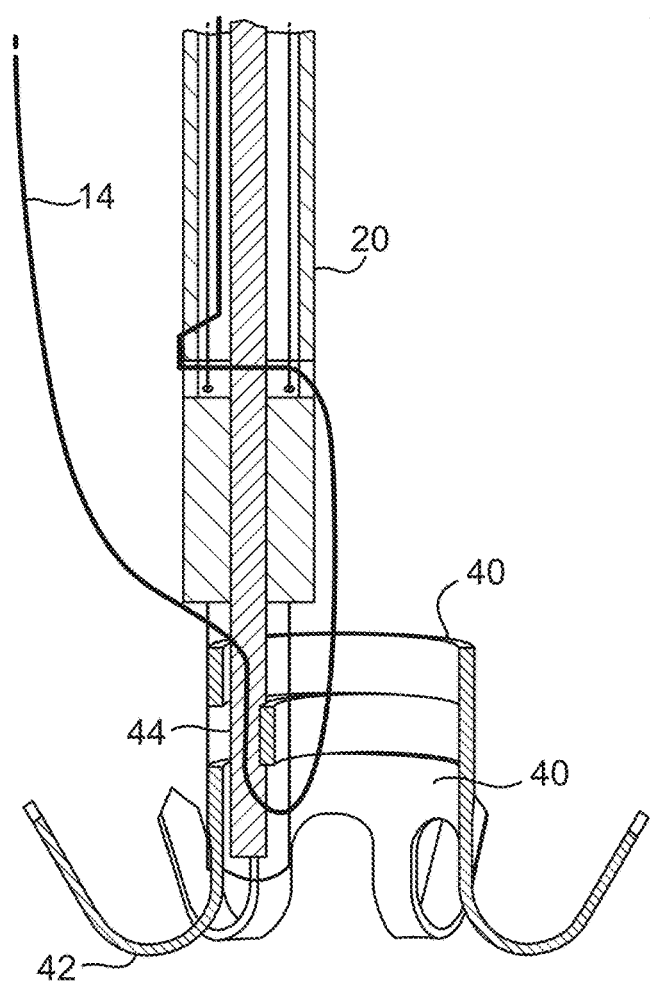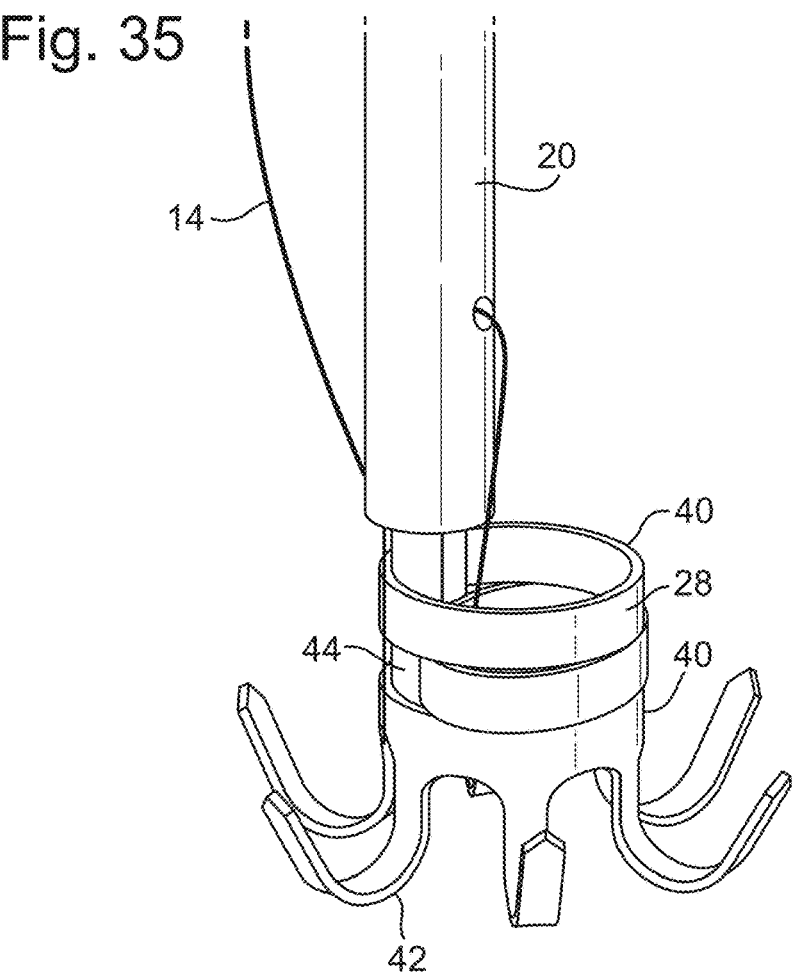
Fig. 35
Fig. 36

DEVICE FOR HEART REPAIR

This application is a 35 U.S.C. § 371 national phase filing of International Application No. PCT/EP2015/071207 filed on Sep. 16, 2015, and further claims priority to United Kingdom Patent Application No. 1416383.6 filed on Sep. 17, 2014, with the contents of the foregoing applications hereby being incorporated by reference herein in their respective entireties.

The present invention relates to a device and a method for implanting an artificial chord in order to repair a heart valve. This disclosure also includes an anchor for implantation within body tissue, which may be used for heart repair.

The chordae tendineae are cord-like tendons that connect the papillary muscles to the tricuspid valve and the mitral valve in the heart. The valves consist of leaflets that open and close with the beating of the heart in order to control blood flow and blood pressure within the heart.

Mitral valve disease presents an important challenge to cardiac surgeons and cardiologists. Mitral regurgitation has become the leading pathophysiological condition of the mitral valve in the developed world. One of the most important causes of regurgitation is prolapse of one of the mitral leaflets. The pathological abnormality that requires repair is rupture or other degenerative changes of the chords. The normal chords can rupture acutely which causes acute decompensation, heart failure. This usually results in an emergency condition requiring rapid intervention. When the chord(s) remain intact, the mitral leaflets open and close synchronously and in a fashion that prevents leakage of the valve. When the chord(s) rupture or get elongated by degenerative processes, then the mitral valve will develop leaks or regurgitation.

Surgical repair of the mitral valve has become relatively standardized, using resection of the prolapsed leaflet or implantation of new, artificial chords to control leaflet motion. In addition a mitral ring is frequently placed to shrink the size of the mitral valve annulus. Surgical replacement of ruptured or elongated chords is highly effective in reducing or minimizing mitral valve regurgitation. The procedure is presently performed with open heart surgery techniques. This requires use of cardiopulmonary bypass and arresting of the heart. This surgical approach, although working well, constitute a highly invasive procedure which can cause serious complications, long hospital stays and substantial expense. Consequently it is much preferred to take a less invasive approach.

Insertion of mitral leaflet chords has been done using a minimally invasive surgical approach entering the heart through its apex. The technique, which was developed by the company Neochord Inc. and is described, for example, in WO 2012/167120, still requires a surgical incision and the chords do not get inserted in the papillary muscles where they normally should be fixed.

WO 2008/101113 describes another example of a system for repair of the heart, including implantation of artificial chords. In the described method an anchor can be attached to the papillary muscle tissue and this is coupled to the leaflet of the mitral valve via an artificial chord, a suture and a clip. The clip allows for adjustment of the length of the artificial chord. A complex multi-stage process is required to implant the papillary anchor and the suture and to join them together. The papillary anchor is formed of a memory metal such as nitinol and has a 'flowered' shape with sharp 'petals' for hooking the anchor to body tissue. The flowered shape is flattened into a tube shape and held in a tube that is passed into the heart. The tube and anchor is then pressed against the papillary muscle and the anchor is pushed out of the tube so that the petals pierce the muscle and fold outward through the muscle to provide a secure coupling of the anchor to the muscle tissue. In a subsequent surgical procedure, an artificial chord may be attached to the anchor. Then in a further procedure, the suture is attached to the leaflet and this suture is joined to the chord by the clip. The suture is attached to the leaflet by locating a vacuum port near to the leaflet and pulling it into the vacuum port where it can be pierced.

It will be appreciated that this technique, whilst avoiding open heart surgery, still requires a sequence of relatively invasive procedures. The number of procedures requires increases the risk to the patient. Furthermore, the complexity of the device means that there are parts implanted within the body that are at risk of coming loose and injuring the patient. In particular, the clip could come loose from the anchors and cause damage internally. It is also thought that the use of a suture with an additional clip, as proposed, may not effectively repair the heart valve since it will not closely simulate a natural chord.

Thus, there is a need for an improved system that will enable repair of the heart by implanting an artificial chord in a minimally invasive procedure.

Viewed from a first aspect the invention provides a catheter device for repair of the heart by implanting an artificial chord, the device comprising: a leaflet anchor for placement in a leaflet of a heart valve, wherein the leaflet anchor is arranged to be coupled to the artificial chord; and a mechanical gripper device for grasping the leaflet of the heart valve, wherein the gripper device comprises a leaflet anchor channel for housing the leaflet anchor in a folded configuration; the gripper device and leaflet anchor being arranged such that when, in use, the gripper device grasps the leaflet, the leaflet anchor can be pushed out of the leaflet anchor channel to pierce the leaflet and form the leaflet anchor into an unfolded configuration so that hooked formations of the leaflet anchor can, in use, secure the leaflet anchor in the leaflet.

This device allows a leaflet to be easily gripped and a new chord securely attached to the leaflet. There is no need for a complex procedure involving the use of vacuum and sutures as in WO 2008/101113. The mechanical gripper device can be opened and closed several times if required to release and re-engage the leaflet until it is in the desired position for the anchor to be placed. The piercing of the leaflet involves a single movement of the leaflet anchor, in contrast to the device of WO 2008/101113, where it is required to first pierce with a needle passing in one direction, and then pull through a suture in the other direction. Thus the device of the first aspect is simpler and more effective than the prior art device.

The mechanical gripper device may include a gripper housing on a main body of the catheter device and a gripper arm rotatably coupled to the gripper housing, so that the gripper arm can open and close to grasp the leaflet between the gripper arm and the gripper housing. The gripper arm may be actuated by a wire pulling on a lever. A spring could be used to pull against the wire and return the gripper arm to the closed position, but in a preferred arrangement there are two wires, one for pulling the gripper arm open and one for pulling it closed.

The leaflet anchor channel can be in the gripper housing or in the gripper arm. It is preferred for it to be in the gripper arm. This means that the leaflet anchor can be easily released from the end of the gripper arm when it has been placed in the leaflet, since the gripper arm can be opened so that the end of the leaflet anchor channel is clear of the catheter device. The gripper housing and the gripper arm may each have a gripping surface between which the leaflet can be clamped. One or both gripping surface(s) may be arranged to hold the leaflet with friction. For example the gripping surface(s) may use a material with a high coefficient of friction and/or the gripping surface(s) may have a texture or surface profile for increasing friction, such as a ridged or saw-toothed profile. The end of the leaflet anchor channel preferably opens into one of the gripping surfaces. The leaflet anchor channel may take the form of a generally cylindrical channel size to be slightly larger than the leaflet anchor in the folded configuration.

It is preferred for the leaflet anchor to be formed from an elastic material and to be arranged so that it assumes the unfolded configuration when no force is applied, and to be able to deform elastically into the folded configuration, for example when constrained within the leaflet anchor channel. The leaflet anchor may be made of a shape memory material, for example a shape memory metal. Nitinol is a preferred material for the leaflet anchor. In one preferred embodiment the leaflet anchor is made from a laser cut nitinol tube. The anchor may be subject to electropolishing after laser cutting in order to remove undesirably rough or sharp edges.

A preferred form for the leaflet anchor is a grapple hook shape, in the unfolded configuration. The leaflet anchor may hence comprise a straight central shaft with a number of hooks spaced apart radially around the shaft. When in the folded configuration the hooks would be straightened out. The leaflet anchor may conveniently be manufactured by cutting a tube to form sharpened tines at one end, which are then bent into the hooks, with the other end of the tube forming the shaft. The shaft may have a diameter that is relatively small compared to the radial extent of the hooks in the unfolded configuration. For example the shaft may have a diameter of 30% or less of the maximum radial extent of the hooks, for example 20% or less. In one example the shaft is 1-2 mm in diameter and the hooks extend over a diameter of about 5-8 mm. If a shape memory material such as nitinol is used then the tines may be bent and heat set into the grappling hook shape after laser cutting of the nitinol tube.

The mechanical gripper device preferably has a leaflet anchor fold-out section with recesses shaped to allow the leaflet anchor to form the unfolded configuration without any hindrance. The recesses may for example be curved so that hooks of the leaflet anchor may curl into the unfolded shape as it is pushed out of the leaflet anchor channel.

It is advantageous if the leaflet anchor can be placed into the leaflet from beneath, i.e. from the side where the papillary muscle is located, so that the new chord may pull the leaflet downward. However, the most convenient route to access the heart involves the catheter entering from above the leaflet. To facilitate the preferred placement of the leaflet anchor from beneath, the catheter device may be arranged so that the open end of the channel is at a proximal end of the gripper device (the 'upper' end when in the heart in the above defined orientation) and the leaflet anchor can be pushed out of the channel moving from the distal end of the catheter device toward the proximal end. In preferred embodiments the catheter device includes a U-shaped rod. This may be a U-shaped piece at the end of a wire that is used to actuate the leaflet anchor. Alternatively it may be a U-shaped rod attached to a separate wire at one end of the U-shape. In either arrangement the free end of the U-shape abuts the end of the leaflet anchor and is arranged to push the anchor toward the proximal end of the catheter device when the wire is pulled. The U-shaped rod should be sufficiently stiff to hold its shape when pulled with force applied to the anchor. In this way the leaflet can be pierced from beneath.

When the leaflet anchor channel is in the gripper arm then the U-shaped rod may extend into the gripper arm. In this case the U-shaped rod needs to be sufficiently elastic to bend when the gripper arm is opened and closed. The U-shaped rod may have a flexible section, for example a section of narrowed cross-section, for aiding the bending motion. The U-shaped rod may also or alternatively be made of a suitably elastic material, which could be nitinol. Advantageously, the elasticity of the U-shaped rod may act as a spring to return the gripper arm to the closed position.

The catheter device may include an artificial chord attached to the leaflet anchor. A hole or eye may be provided in the leaflet anchor for attachment of the chord. In preferred embodiments the chord is joined in the catheter device to a wire that enables it to be pulled or pushed. The use of such a wire allows for shortening and lengthening adjustments to the chord. The chord may be a Gore-Tex® suture or other appropriate biocompatible material, such as a thin nitinol wire, an ultra-high-molecular-weight polyethylene (UHMWPE) wire, or a composite wire comprising a tough core such as nitinol or high strength suture and an outer coating such as PTFE or ePTFE. In a preferred embodiment the catheter device also holds a papillary anchor for attachment to the papillary muscle. The chord may extend from the leaflet anchor to the papillary anchor. The papillary anchor may take a similar form to the anchor disclosed in WO 2008/101113, although it is preferred to use an improved design as described below. In preferred embodiments the chord joins the two anchors together directly, with no intervening clip as in WO 2008/101113. This means that the artificial chord can more closely emulate the natural chords, and so the repair to the heart is more effective.

It is preferred for the papillary anchor to be formed from an elastic material and to be arranged so that it assumes an unfolded position when no force is applied, and to be able to deform elastically into a folded position, for example when constrained within a papillary anchor housing of the catheter device. The device may be arranged so that the papillary anchor can be push out of the papillary anchor housing in order to pierce the papillary muscle with the hooks and to securely engage the anchor with the muscle as the hooks curl into the unfolded position. The papillary anchor may be made of a shape memory material, for example a shape memory metal. Nitinol is a preferred material for the papillary anchor. In one preferred embodiment the papillary anchor is made from a laser cut nitinol tube.

The papillary anchor may include a number of hooks for piercing and engaging with the tissue of the papillary muscle. A grappling hook shape is possible, similar to the leaflet anchor, but the preferred design for the papillary anchor uses a slightly wider tube section relative to the extent of the hooks. Thus in a preferred embodiment the papillary anchor includes a tube section with a number of hooks extending from one end of the tube, wherein the hooks extend across a diameter that is less than three times the diameter of the tube, for example about twice the diameter of the tube.

Similarly to the leaflet anchor, the papillary anchor may conveniently be manufactured by cutting a tube to form sharpened tines at one end, which are then bent into the hooks, with the other end of the tube forming the body of the anchor. If a shape memory material such as nitinol is used then the tines may be bent and heat set into the hook shape after laser cutting of the nitinol tube. The anchor may be subject to electropolishing after laser cutting in order to remove undesirably rough or sharp edges.

Preferably the papillary anchor is provided with a mechanism for releasably clamping the artificial chord. In one example, the papillary anchor is provided with a locking mechanism that clamps the chord when no force is applied, and that can be elastically deformed to release the chord for adjustment of the length of the chord during implantation thereof. This means that after the leaflet anchor and the papillary anchor are implanted then the new chord can be tensioned appropriately, whilst monitoring heart function, to ensure that the repair is effective, and then the chord can be clamped by releasing the force on the anchor. After implantation, since the locking mechanism clamps the chord when no force is applied, then the chord will be held between the leaflet and the papillary muscle with the right tension.

The preferred arrangement for the papillary anchor, with the locking segment, is considered to be new and inventive in its own right and can be utilised for various other purposes, such as in place of the anchor described in WO 2008/101113. Therefore, viewed from a second aspect, the invention provides an anchor for implantation in body tissue to hold a line, the anchor comprising a number of hooks for engagement with the body tissue and having a folded position and an unfolded position, wherein the anchor is made of an elastic material such that it can be elastically deformed into the folded position by application of a constraining force, and will return to the unfolded position when no constraining force is applied, the anchor further comprising a locking mechanism for clamping the line when no force is applied, and being able to be elastically deformed to release the line from the locking mechanism for adjustment of the length of the line.

This anchor has the advantage that during implantation of the anchor the locking mechanism can be held open and the line adjusted in length, and then after implantation, since the locking mechanism clamps the line when no force is applied, then the line will be securely held in place. This anchor may of course advantageously be used in heart repair to attach a line such as an artificial chord to the heart tissue, and thus could be used to repair a valve of the heart as discussed herein. The anchor may be a papillary anchor for securing an artificial chord to the papillary muscle. Alternatively it may be an anchor for attachment to a valve or a leaflet of a valve, or for attachment to the heart wall. The anchor could be used to fix sensors or pacemakers inside the heart cavities. It could also be used to fix sensors or for other procedures inside other parts of the body, for example within the gastrointestinal tract or the urinary bladder. The anchor will provide advantages for any procedure where a line such as a chord, cable, suture or wire, needs to be secured to body tissue.

The anchor may have any or all features described above in relation to the papillary anchor that may be used with the device of the first aspect. For example it may be formed of a nitinol tube cut to form tines which are then bent and heat set to form the hooks.

The locking mechanism may comprise a resiliently deformable locking segment formed in a wall of the anchor and divided from the wall by one or more slit(s). The anchor may be arranged so that when no forced is applied then the slits are closed with no gap or a relatively narrow gap in order to clamp the line, whereas when a suitable force is applied to the locking segment and/or wall then the locking segment and/or the wall will elastically deform to widen the opening provided by the slit(s) so that the line is released. The anchor may have a tubular body section, in which case the locking segment may be formed in the wall of the tube. The locking segment may be a band with parallel slits on two sides, such that the band can be pulled out of plane with the wall by application of a force in order to open up the slits.

Such a locking segment can be held open by sliding a holder into the slit(s). The anchor may be used in a system comprising an anchor housing for holding the anchor in the unfolded position prior to implantation, a holder for holding the locking mechanism open, a line, and the anchor attached to the line.

In one example arrangement the anchor comprises one or more hole(s) for routing the line, for example there may be a hole in the body of the anchor between the locking mechanism and the hooks. The use of a hole can increase the options for how the line can be routed, which means that different levels of friction can be provided.

The invention extends to the anchor in combination with a line. The line may be looped once or multiple times through the slit(s). Different arrangements for the line can provide different levels of friction. The line may be a Gore-Tex® suture, for example for used as an artificial chord for repair of the mitral valve.

It is important that the line is held with an appropriate level of friction, but that it is not at risk of cutting or fraying. The slit(s) may be shaped to provide increased friction for example by having a wavy or saw tooth profile. When the anchor is made of laser cut nitinol then it is highly preferred for it to be treated by electropolishing afterward since this will remove any sharp edges from the slit(s) and reduce the risk of fraying or cutting the line.

The use of electropolishing to mitigate the risk of fraying and/or cutting, and to provide an anchor able to clamp firmly without cutting is considered important. The invention extends in another aspect to a method of manufacturing an anchor as defined in the second aspect, the method comprising laser cutting a tube, preferably a shape memory metal tube such as nitinol, and then electropolishing after the laser cutting.

There are significant benefits to the use of the anchor with locking mechanism as a papillary anchor paired with the catheter device of the first aspect. Hence, in a third aspect, the invention provides a catheter device for repair of the heart by implanting an artificial chord, the device comprising: a leaflet anchor for placement in a leaflet of a heart valve, wherein the leaflet anchor is arranged to be coupled to the artificial chord; a mechanical gripper device for grasping the leaflet of the heart valve, wherein the gripper device comprises a leaflet anchor channel for housing the leaflet anchor in a folded configuration; a papillary anchor for placement in a papillary muscle of the heart and arranged to be coupled to the artificial chord, the papillary anchor comprising a number of hooks for engagement with the papillary muscle and having a folded position and an unfolded position, wherein the papillary anchor is made of an elastic material such that it can be elastically deformed into the folded position by application of a constraining force, and will return to the unfolded position when no constraining force is applied, the papillary anchor further comprising a locking mechanism for clamping the chord when no force is applied, and being arranged to be elastically deformed to release the chord from the locking mechanism for adjustment of the length of the chord; a papillary anchor housing at a distal end of the device for holding the papillary anchor in the folded position; and a holder for releasably holding the locking mechanism open; the gripper device and leaflet anchor being arranged such that when, in use, the gripper device grasps the leaflet, the leaflet anchor can be pushed out of the leaflet anchor channel to pierce the leaflet and form the leaflet anchor into an unfolded configuration so that hooked formations of the leaflet anchor can, in use, secure the leaflet anchor in the leaflet; the papillary anchor and papillary anchor housing being arranged such that when, in use, the distal end of the device is pressed against the papillary muscle, the papillary anchor can be pushed out of the papillary anchor housing so that the hooks of the papillary anchor can pierce and engage with the papillary muscle as they return to the unfolded position; and the holder and locking mechanism being arranged so that the locking mechanism can be held open during placement of the papillary anchor, and during adjustment of length of the chord, and then closed by removal of the holder once the chord adjustment is completed.

This catheter device may optionally have any or all features described above in connection with the first aspect and/or the second aspect.

The invention also extends to use of the catheter device of the first aspect, the anchor of the second aspect, the system with the anchor, or the catheter device of the third aspect for heart repair. It is preferred for use of the catheter device/anchor to take an endovascular approach to the heart.

Viewed from a fourth aspect, a method of heart repair comprises: introducing a catheter device to the heart endovascularly, the catheter device being as described in the third aspect above and also including an artificial chord; grasping a leaflet of the mitral valve with the mechanical gripper device; pushing the leaflet anchor out of the channel to pierce the leaflet and engage the leaflet anchor with the leaflet; moving the catheter device away from the leaflet with the gripper device open in order to release the leaflet anchor from the catheter device; locating the end of the papillary anchor housing at the papillary muscle; pushing the papillary anchor out of the papillary anchor housing in order to engage the papillary anchor with the papillary muscle; adjusting the length of the chord; removing the holder from the locking mechanism in order to clamp the chord; releasing the chord from the catheter device; and withdrawing the catheter device from the body.

The chord may be released by uncoupling it from a wire or the like that holds it during the implantation and adjustment. Or it may be cut in order to minimise the excess chord that is left in the body. The method may include using a catheter device with features as set out above in relation to optional and/or preferred features for the first aspect.

Certain preferred embodiments of the invention will now be described by way of example only and with reference to the accompanying drawings in which:

FIGS. 1 to 3 show a catheter device for repair of a heart valve;

FIGS. 33 to 36 illustrate interaction of the papillary anchor with the chord and a locking and cutting piece of the catheter device;

Figure 4:
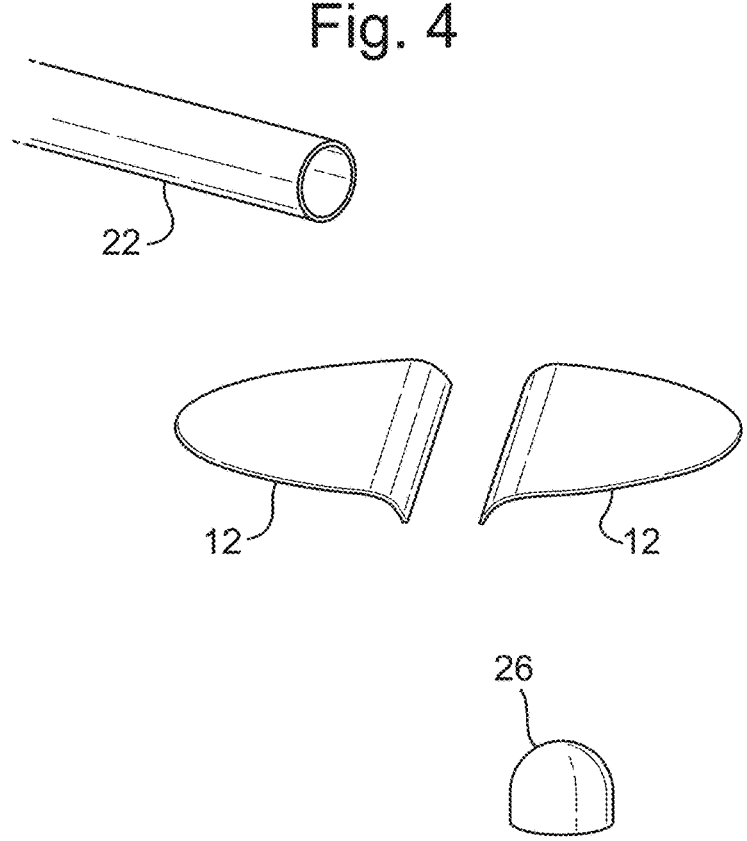
FIGS. 4 to 7 illustrate the procedure for insertion of the catheter device through a mitral valve, and gripping of a leaflet of the mitral valve with the device.

The new catheter device presented here is proposed for non-surgical (endovascular) insertion of mitral chords to address mitral regurgitation caused by prolapse of a leaflet 12 of the valve. The chords are fixed to the prolapsing leaflet 12 and to the papillary muscle 26, thereby recreating a normal anatomy. A single device is used to place both a leaflet anchor 10 and a papillary anchor 9. The length of the chord 14 can be adjusted, again using the same device, to eliminate the mitral regurgitation. Thus, the new device enables a single minimally invasive endovascular procedure to be used to repair the mitral valve, providing significant advantages compared to earlier systems requiring more invasive procedures and/or multiple operations.

It should be noted that although an endovascular approach is preferred and the device is hence capable of using this approach, the device could of course be used in different procedures, including more invasive procedures. Many of the advantages will remain, and it could be beneficial to use this device in situations where a more invasive procedure is merited. In addition, it is contemplated that, as discussed above, aspects of the design of the papillary anchor 9 could be used for an anchor for other purposes and this disclosure is not intended to be limited in this regard.

The new device described in the following can be used to insert mitral chords through the venous system, starting in the femoral vein in the groin. A catheter is advanced to the right atrium. Approach to the left atrium is then gained by a so-called transseptal puncture whereafter a larger guidance catheter is advanced into the left atrium. The catheter device for the heart repair is then introduced through the guiding catheter and into the left atrium.

X-ray and ultrasound guidance is used to position the device and, as explained in more detail below, the mitral leaflet 12 is grabbed and a new chord 14 is attached using a self-expandable anchor. The chord is then attached to the papillary muscle 26, using a second anchor. The chord length can now be adjusted to eliminate any mitral regurgitation. Excess chord is then cut and all catheters are withdrawn. Echo and Doppler imaging is used to perform the procedure and monitor the result. The successful use of this endovascular technique will drastically reduce the invasiveness, complications and cost of mitral valve repair.

More detail on the structure and function of the device is set out below with reference to the Figures. The procedure of using the device can be summarised as follows:

1) The femoral vein is entered using standard Seldinger technique and the guiding catheter introduced.

2) The guiding catheter is advanced to the right atrium under x-ray guidance.

3) The left atrium is entered after penetration of the atrial septum, guided by x-ray and transesophageal echo.

4) Correct position of the entrance site in the left atrium is verified to assure proper alignment for insertion of the guiding and treatment catheters. The entrance hole in the atrial septum is dilated and the guiding catheter is advanced into the left atrium.

5) A treatment catheter is advanced through the guiding catheter and positioned in the left atrium above the mitral valve.

6) The prolapsing segment of the mitral leaflet 12 is located with ultrasound and the treatment catheter is advanced into the left ventricle placing a gripper of the treatment catheter in position to grip the prolapsing segment.

7) The prolapsing segment is gripped and after assuring correct position the leaflet anchor 10 is pushed through the leaflet 12 allowing it to open and fix the leaflet 12.

8) The leaflet anchor 10 is disengaged from the treatment catheter and the catheter is advanced further into the left ventricle until it makes contact with the papillary muscle 26.

9) The papillary anchor 9 is pushed into the papillary muscle 26 and the covering sheath pulled back thereby letting the anchor open inside the papillary muscle 26.

10) The length of the artificial chord 14 is adjusted until mitral regurgitation is eliminated.

11) The treatment catheter is pulled back to the left atrium, leaving an adjustment catheter 20 holding the papillary anchor 9, and elimination of mitral regurgitation is again confirmed by echocardiography.

12) An adjustment pin of the adjustment catheter 20 is withdrawn, locking the artificial chord 14 inside the papillary anchor 9.

13) The excess chord is cut using a cutting device of the adjustment catheter 20.

14) Additional chords may be placed if necessary.

15) The treatment and guiding catheter is withdrawn and removed from the vascular system.

FIGS. 1, 2 and 3 show a part of the treatment catheter. The treatment catheter is composed of four different main parts; a steerable catheter 2 (not shown in this Figure), gripper housing 4, gripper arm 6 and papillary anchor housing 8, which holds a papillary anchor 9. The steerable catheter could be replaced with an alternative arrangement using a steerable sheath about a steerable catheter and flexible tubing within the steerable catheter.

FIG. 1 shows a front view with the gripper arm 6 closed. FIG. 2 shows an oblique view, again with the gripper arm 6 closed. FIG. 3 is a side view with the gripper arm 6 open.

Inside the gripper arm 6 there is a leaflet anchor 10, which can be pushed out, after the leaflet 12 is grasped. FIGS. 23 to 29 show more detail of the leaflet anchor 10, as described below. The leaflet anchor 10 is connected to an artificial chord 14, which sits inside a narrow channel that goes along the surface of the gripper arm 6 and papillary anchor housing 8. The channel is slightly smaller than the diameter of the new chord 14. This makes the chord 14 sit in place due to a friction fit. The new chord 14 goes into the papillary anchor housing 8 and through a papillary anchor locking section, through a locking and cutting piece 18, and through an adjustment catheter 20. These parts are described in further detail below with reference to FIGS. 30 to 36. The new chord 14 is attached to a wire which passes back along the catheter all the way to the outside (to make the adjustment smoother). The wire allows for a shortening of the chord during the procedure, by pulling, or a lengthening of the chord, since the wire can be pushed through the catheter.

The treatment catheter is approximately 6-7 mm in diameter, and approximately 30 mm in length (without the steerable catheter 2).

Figure 5:
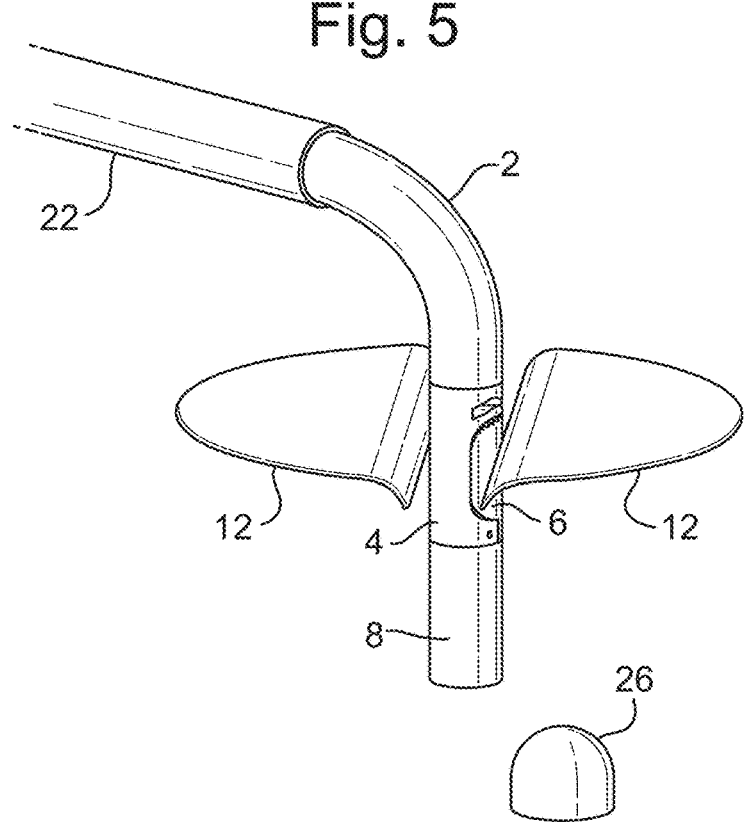

FIGS. 4 to 7 illustrate the procedure for insertion of the catheter device through a mitral valve, and gripping of a leaflet 12 of the mitral valve with the device. The procedure starts with placing a soft guide catheter 22 (approximately 24 french/8 mm diameter) into the atrium using standard techniques. FIG. 4 shows this, with the mitral valve shown schematically as a pair of leaflets 12 below the guide catheter 16. The treatment catheter is passed along the guide catheter and then placed between the two leaflets 12, with the gripper 6 adjacent the leaflet 12 of interest, i.e. the prolapsed leaflet 12, as shown in FIG. 5. The gripper 6 is now ready to grasp the leaflet 12. The correct position is confirmed by 3D ultrasound and/or other available sources.

Figure 6:
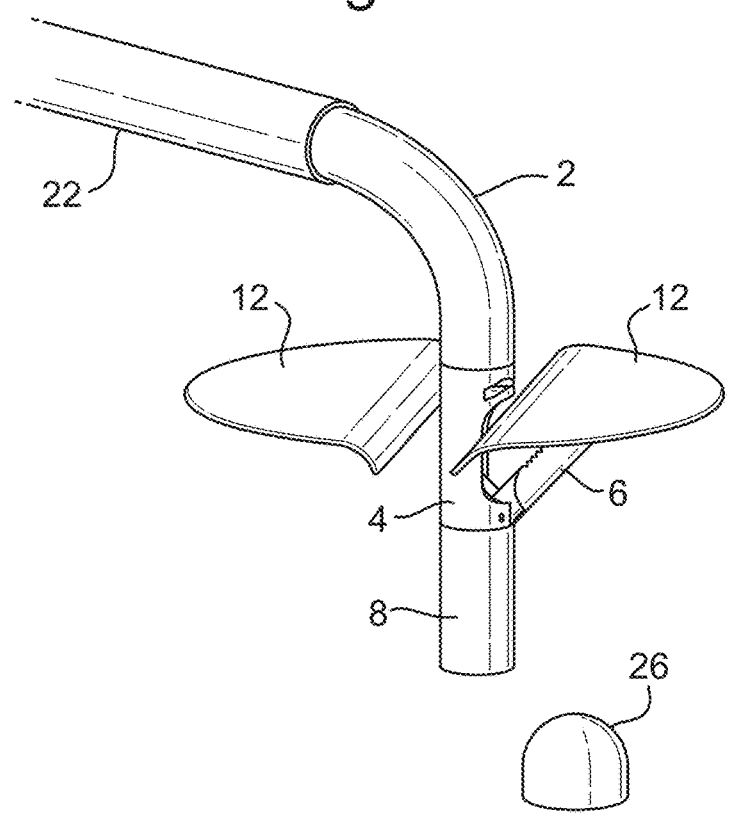
Figure 7:
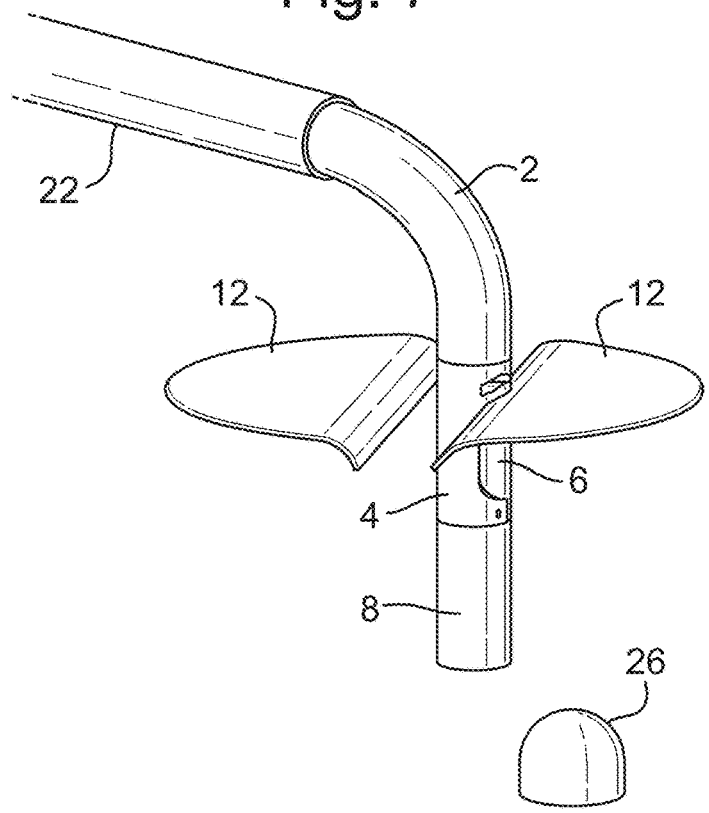

The gripper arm 6 is opened beneath the leaflet 12, with the treatment catheter in the correct position, as shown in FIG. 6, and then closed so that it grips the leaflet 12 to the main part of the catheter, as shown in FIG. 7. A ridged surface on the gripper arm 6 helps it grip the leaflet 12. 3D ultrasound and/or other available sources are used to confirm that the gripper 6 has grasped the correct part of the leaflet 12.

Figure 8:
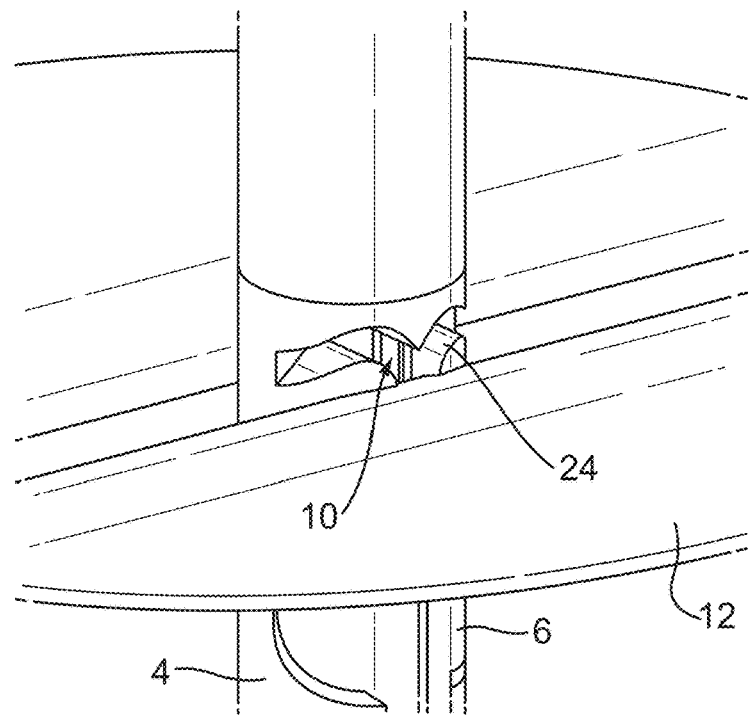
FIGS. 8 and 9 show a close up view of the valve during placement of a leaflet anchor, which is coupled to an artificial chord.
Figure 9:
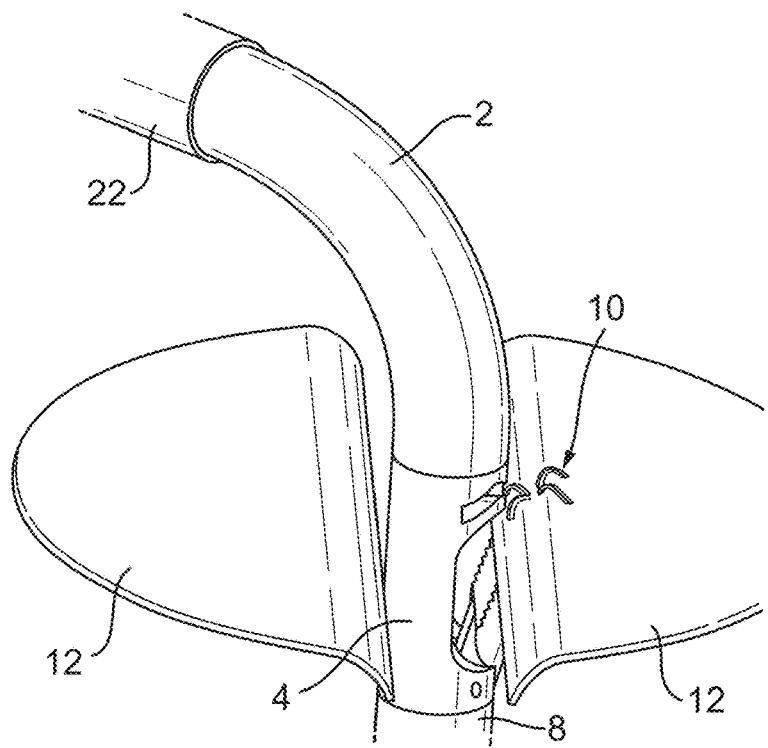

The gripper 6 can be opened and closed as many times as needed to grasp the right part of the leaflet 12. The opening and closing is facilitated by a system allowing for one wire to pull the gripper arm 6 open, and one to pull it closed. Once the position of the gripper 6 is confirmed then the leaflet anchor 10 can be pushed out of the end of the gripper 6 by pulling a wire in the other end of the catheter. The leaflet anchor 10 goes through the leaflet 12 and folds out in the top part of the treatment catheter in a leaflet fold-out section 24. The gripper is then opened and this releases the leaflet anchor 10 from the catheter, leaving it placed in the leaflet 12. FIG. 8 shows a close up view of the gripper 6 holding the leaflet 12, and FIG. 9 shows the leaflet anchor 10 placed in the leaflet 12. A more detailed description of the leaflet anchor 10 and the process of placing the anchor 10 in the leaflet 12 is set out below in relation to FIGS. 21 to 29.

Figure 10:
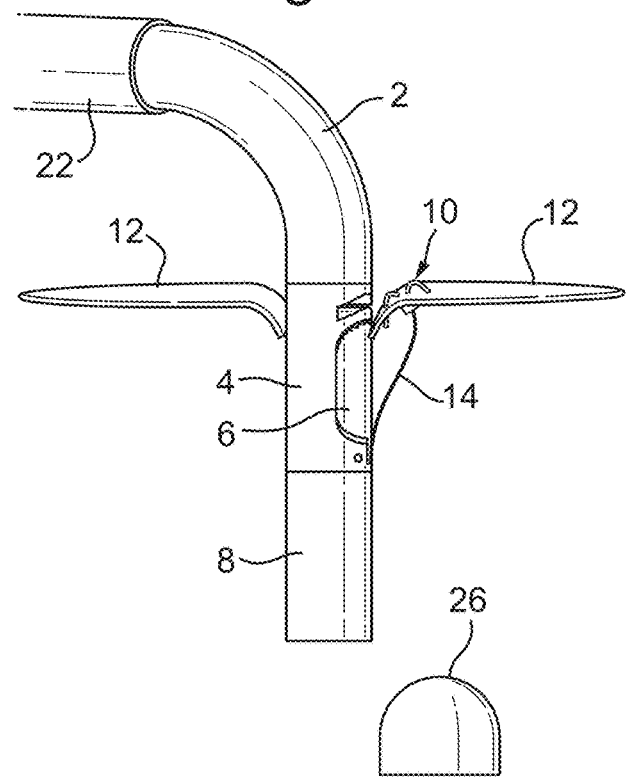
FIGS. 10 to 12 show movement of the catheter device to the papillary muscle and placement of a papillary anchor, which is joined to the leaflet anchor by the artificial chord.
Figure 11:
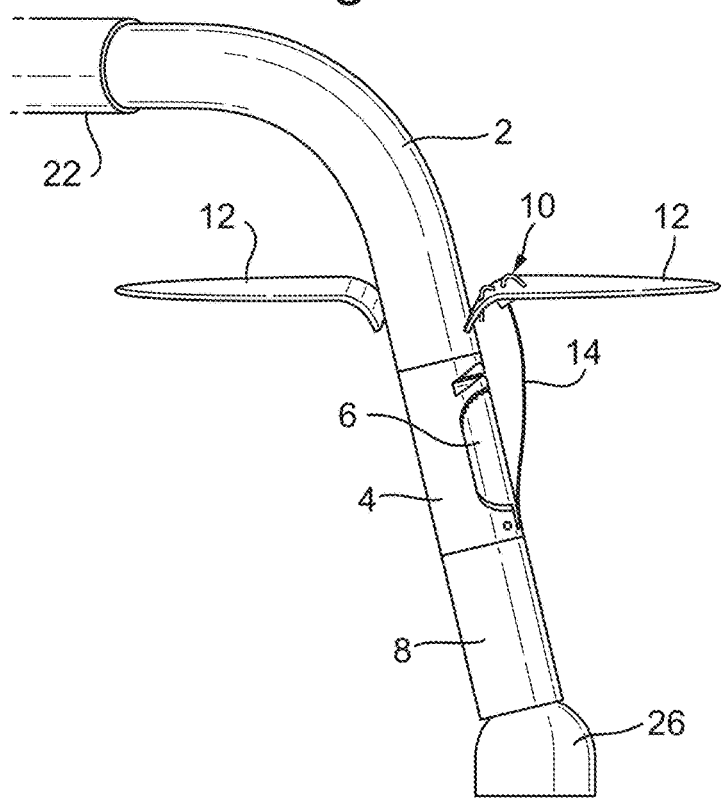
Figure 12:
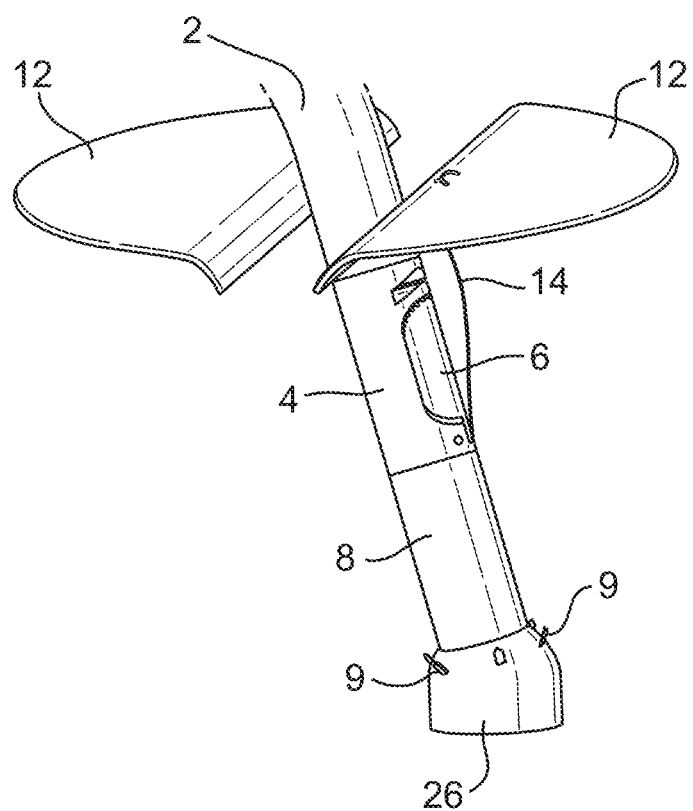

With the leaflet anchor 10 placed, the gripper 6 is closed, and the treatment catheter is placed between the leaflets 12 again. FIGS. 10 to 12 show movement of the catheter device to the papillary muscle 26, shown schematically as a dome shape, and placement of the papillary anchor 9, which is joined to the leaflet anchor 10 by the artificial chord 14.

The heart is of course still beating and the movement of the leaflet 12 will continue to pull the chord 14 loose from its channel in the catheter. This is shown in FIG. 10. More chord can be supplied through the guide catheter while the treatment catheter is on its way down to the papillary muscle 26.

The papillary anchor housing 8 at the end of the treatment catheter is then placed onto the papillary muscle 26 as shown in FIG. 11. The position can be confirmed by 3D ultrasound and/or other available sources. Once the position is confirmed, the adjustment catheter 20 pushes out the papillary anchor 9 into the papillary muscle 26. The papillary anchor 9 folds out inside the muscle 26, as shown in FIG. 12.

Figure 13:
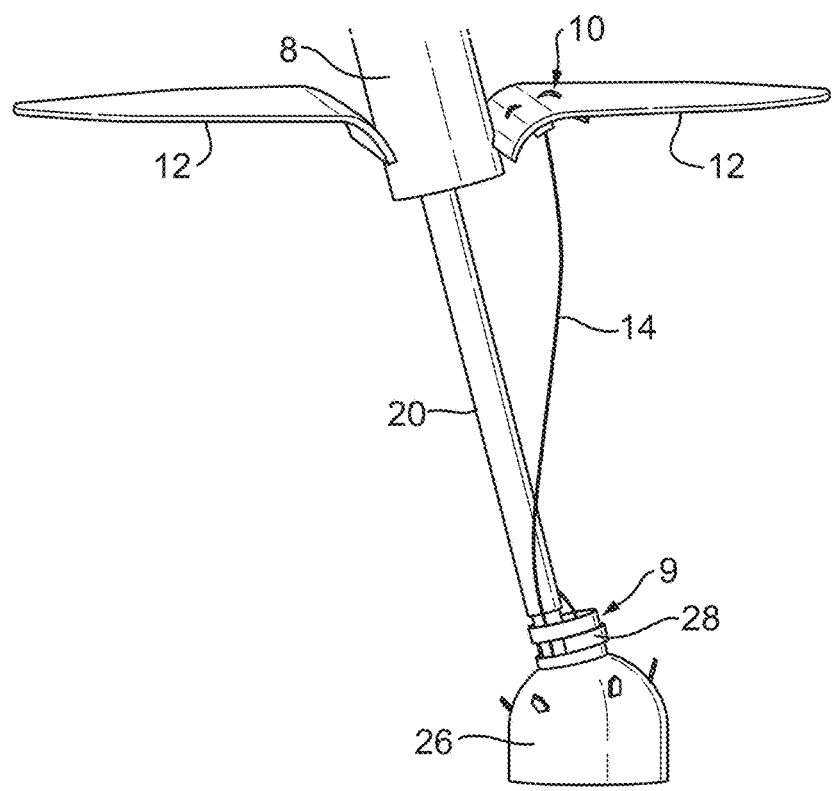
FIGS. 13 and 14 illustrate withdrawal of a treatment catheter part of the device and adjustment of the chord length with an adjustment catheter.
Figure 14:
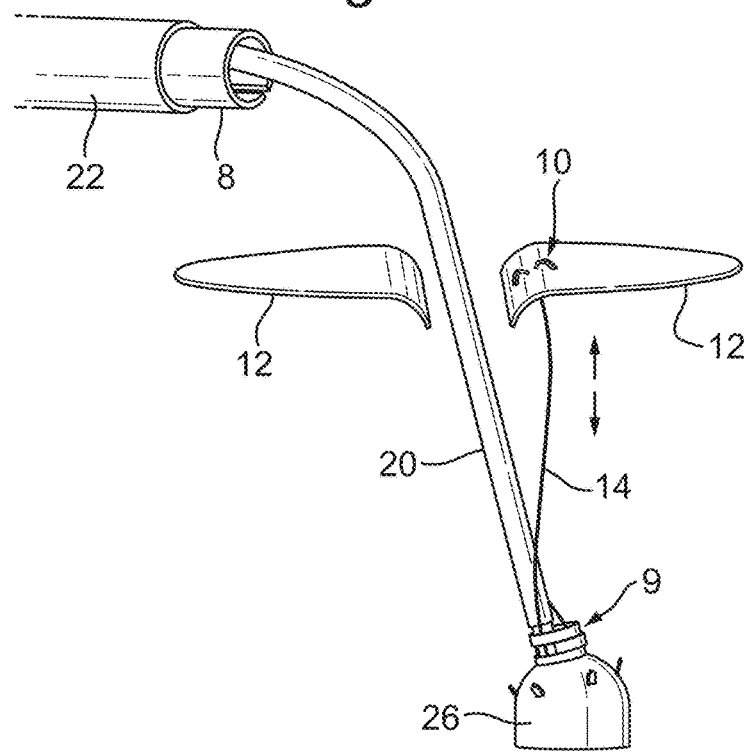

FIGS. 13 and 14 show the next steps. The treatment catheter is retracted into the guide catheter to minimize influence on the moving leaflets 12. The adjustment catheter 20 remains at the papillary anchor 9. It is approximately 2 mm in diameter. The length of the chord 14 is now adjusted with a wire from the outside (the wire is connected to the new chord 14 inside the adjustment catheter 20 as explained above). The chord length is continuously adjusted and the functioning of the leaflet 12 is monitored. The length of the chord 14 can be reduced by pulling the chord wire back through the catheter. The length can also be increased by pushing the chord wire, which will slacken the chord 14 and allow the movement of the leaflet 12 to pull it out of the adjustment catheter 20. The small size of the adjustment catheter 20 means that the effect of the device on the functioning of the leaflet 12 is minimised. The right length for the chord 14 is confirmed with 3D ultrasound and/or other available sources.

Figure 15:
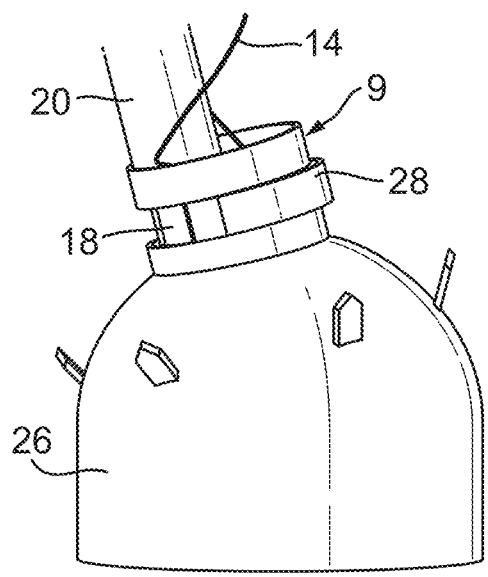
FIGS. 15 to 18 show the procedure for locking of the chord, cutting the chord, and release of the adjustment catheter from the papillary anchor.
Figure 16:
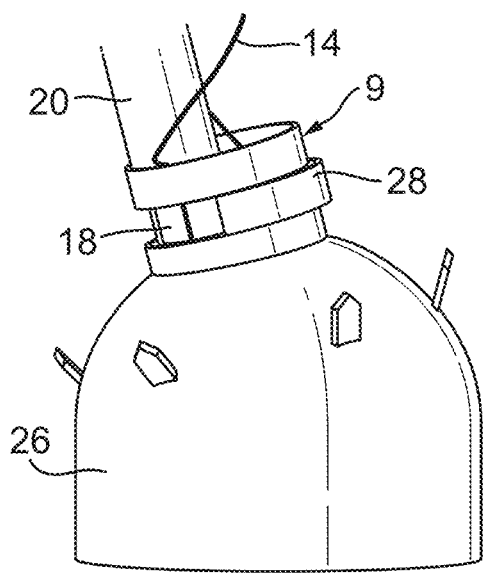
Figure 17:
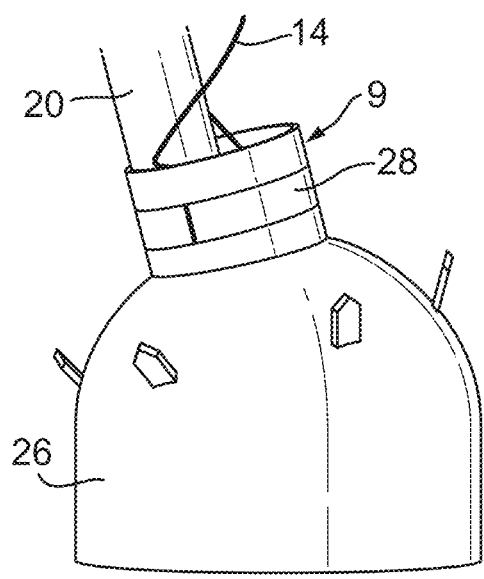
Figure 18:
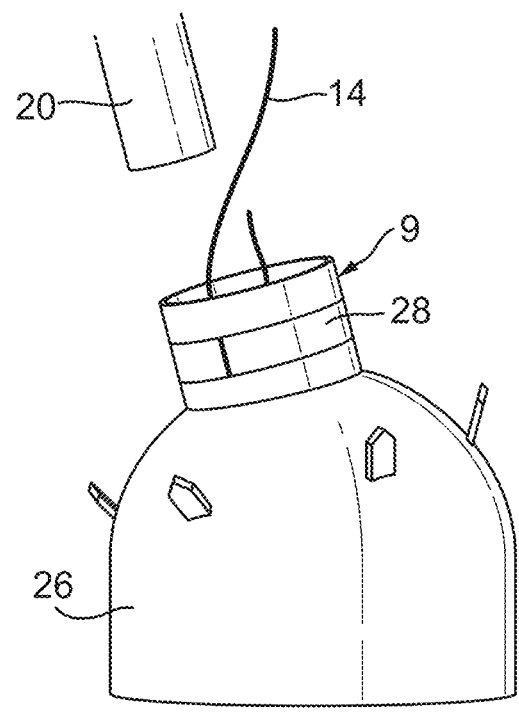

When the correct length is confirmed then the device is disengaged from the papillary anchor 9 as shown in FIGS. 15 to 18. This process also locks the chord 14 in place and cuts off any excess, which is retained in the catheter and withdrawn from the body when the catheter is removed. FIG. 15 shows the adjustment catheter 20 still in place, with the locking and cutting piece 18 holding a locking segment 28 of the papillary anchor 9 open. The locking and cutting piece 18 is retracted, as shown in FIG. 16, while still doing small adjustments to the chord length for optimisation. The locking and cutting piece 18 will first release the locking segment 28, as shown in FIG. 17, and then cut the chord 14. The locking segment 28 is a band of the papillary anchor 9 that can be flexed to open a gap for the chord 14 to pass through. In the natural shape of the papillary anchor 9, when no forced is applied, this locking segment 28 fits closely with the remainder of the anchor 9 and so it will hold the chord 14 in place. The locking and cutting piece 18 of the adjustment catheter 20 is used to hold the locking segment 28 open until the chord 14 is the correct length. A blade within the locking and cutting piece 18 cuts the chord 14, which is pulled against the blade when the adjustment catheter 20 is withdrawn from the papillary anchor 9. More detail of the papillary anchor 9 and the locking and cutting piece 18 is set out below with reference to FIGS. 30 to 36.

The device includes a safety wire (not shown) that acts to prevent the papillary anchor 9 from escaping into the body in the event that it is not correctly placed. The safety wire is a wire that starts on the outside, goes through the adjustment catheter 20 around the papillary anchor 9, and outside again through the adjustment catheter 20. Once the locking and cutting have been done, and the papillary anchor 9 is seen to be secured to the papillary muscle 26 and to the leaflet anchor 10 then the safety wire is pulled out. The adjustment catheter 20 can now be retracted into the treatment catheter. The treatment catheter, and the guide catheter is then removed and the procedure is complete.

Figure 19:
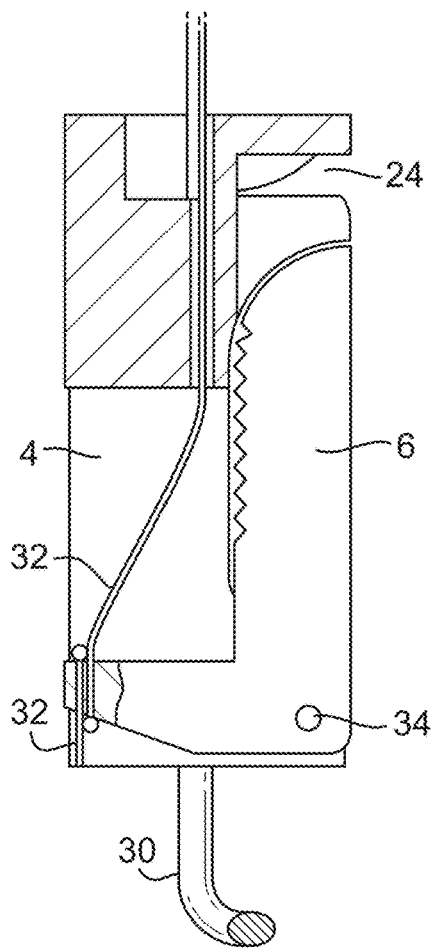
FIGS. 19 and 20 show further detail of a gripper for gripping the leaflet during placement of the leaflet anchor.
Figure 20:
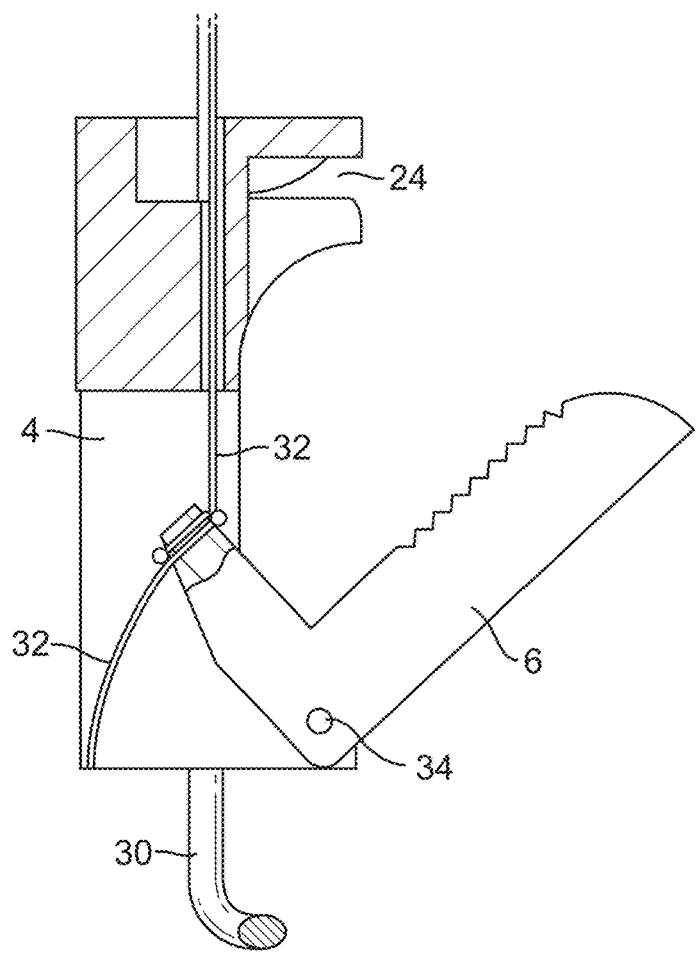

FIGS. 19 and 20 show further detail of the gripper 6 and the related parts for gripping the leaflet 12 during placement of the leaflet anchor 10. The gripper section of the catheter device consists of the gripper housing 4, gripper arm 6, nitinol U-rod 30 (shown only partially in FIGS. 19 and 20), and two wires 32 to operate the gripper arm 6. The gripper arm 6 has a hinge 34 in the front part of the gripper housing 4. The gripper arm 6 is connected to the two wires 32. The wires 32 can be pulled to open and close the gripper arm 6, as shown. The closing wire goes over a pulley. The surface of the gripper arm 6 has high friction, so that the leaflet 12 will "stick" to it. The part of the gripper housing 4 adjacent the gripping face of the gripper will also have friction surface to ensure good grasping.

Figure 21:
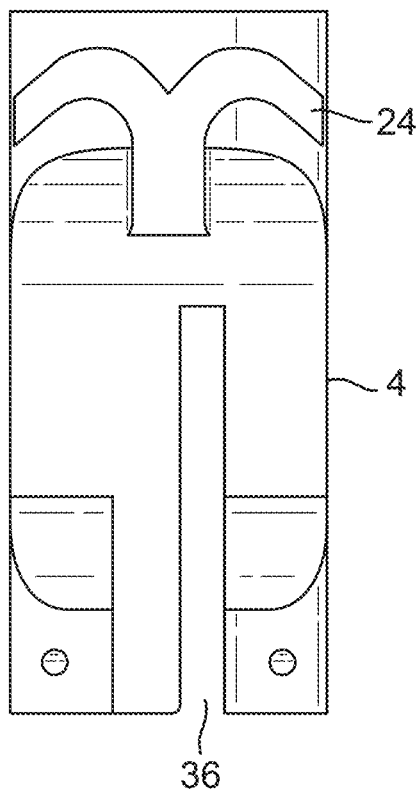
FIG. 21 shows the gripper housing in close up view.

The gripper housing 4 is shown in close up view in FIG. 21. The gripper 6 has an asymmetrical shape so that it fits into an offset recess 36 in the gripper housing 4. This is to make room inside the gripper housing 4 for other channels, for example for the chord 14 and wires 32. The hinge 34 is a simple rod fitted through holes in the gripper housing 4 and a corresponding hole through the gripper arm 6. The upper part of the gripper housing 4 has an anchor fold-out section 24, with curved grooves to accommodate the movement of the leaflet anchor 10 from its stowed configuration into its deployed/implanted shape.

Figure 22:
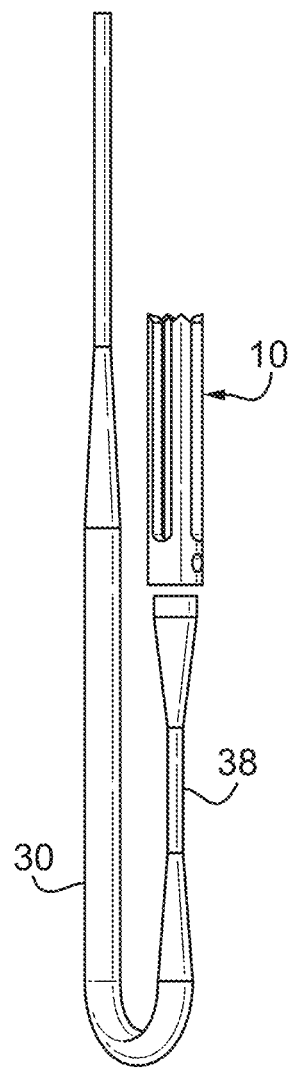
FIG. 22 shows the leaflet anchor in its stowed configuration, along with a U-rod that deploys the leaflet anchor.

It is important to understand that the leaflet anchor 10 is not deformed plastically by the anchor fold-out section 24. Instead, the leaflet anchor 10 is formed with a shape including the required curved hook sections, and then deformed elastically when it is stowed within the gripper arm 6. When the leaflet anchor 10 is pushed out of the gripper arm 6 then it simply returns elastically to its natural shape. FIG. 22 shows the leaflet anchor 10 in its stowed configuration, being the shape it is forced into when held inside the gripper 6. FIG. 22 also shows the U-rod 30 that deploys the leaflet anchor 10. This U-rod 30 is partly within the gripper 6 and partly within the main part of the catheter.

The leaflet anchor 10 and U-rod 30 are shown within the catheter and gripper 6 in FIGS. 23 to 26, which illustrate the process of gripping the leaflet 12 and placing the leaflet anchor 10. The U-rod 30 has a bendable section 38 so the gripper can open and close, while the U-rod 30 is inside. Advantageously, this bendable section 38 can act as a sort of a spring, applying a restoring force to return the gripper 6 to the closed position. The U-rod 30 is made of a material with the ability to deform elastically to a high degree in order to allow for the bending of the bendable section. Suitable materials include shape memory materials, for example shape memory metals such as nitinol. A shape memory metal also has the advantage that the U-rod 30 can be made stiff, which makes the transfer of force with the U-rod 30 more efficient. The U-rod 30 may consist of a thin nitinol wire and tubes on the outside of the wire, to make the U section stiffer. Alternatively, the U-rod 30 could be made of several types of materials to achieve the required properties.

Figure 23:
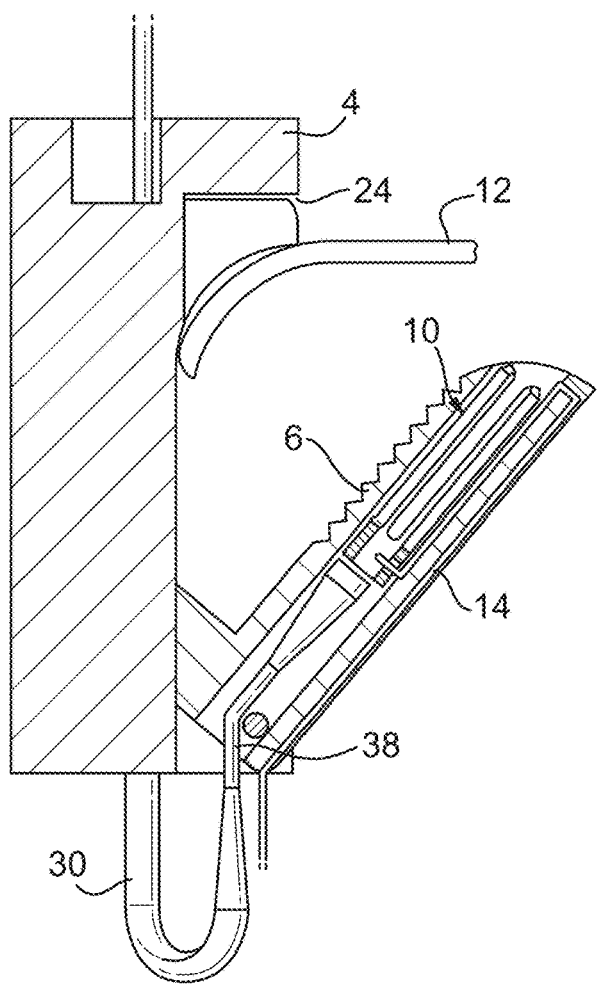
FIGS. 23 to 26 illustrate the process of gripping the leaflet and placing the leaflet anchor.
Figure 24:
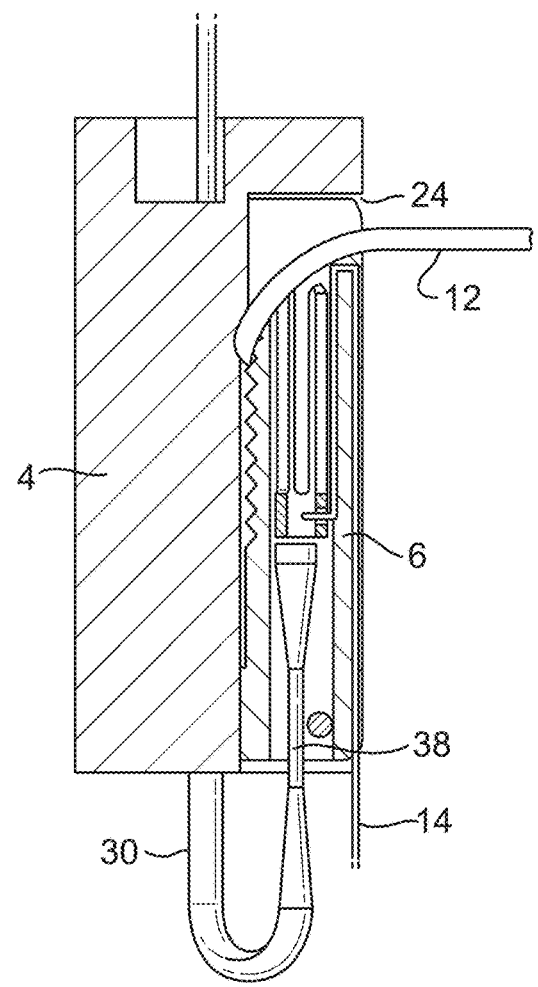
Figure 25:
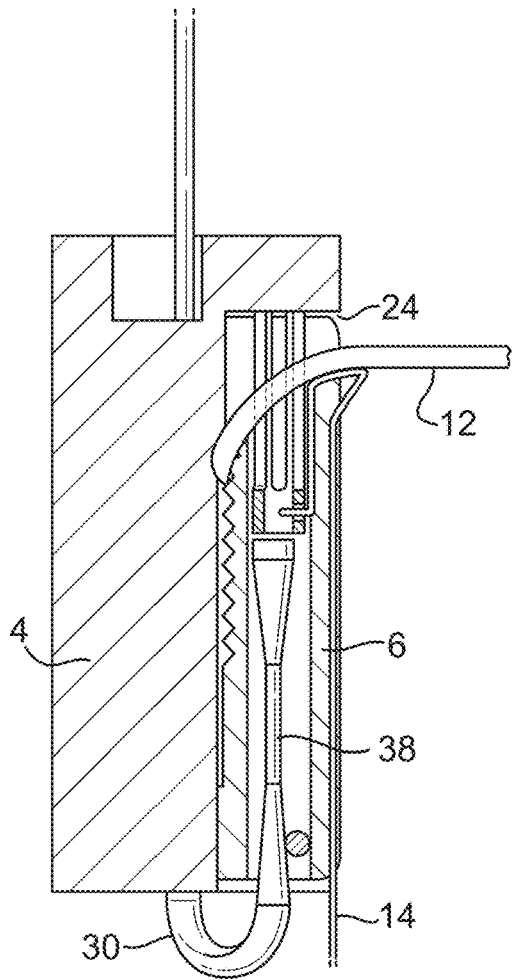
Figure 26:
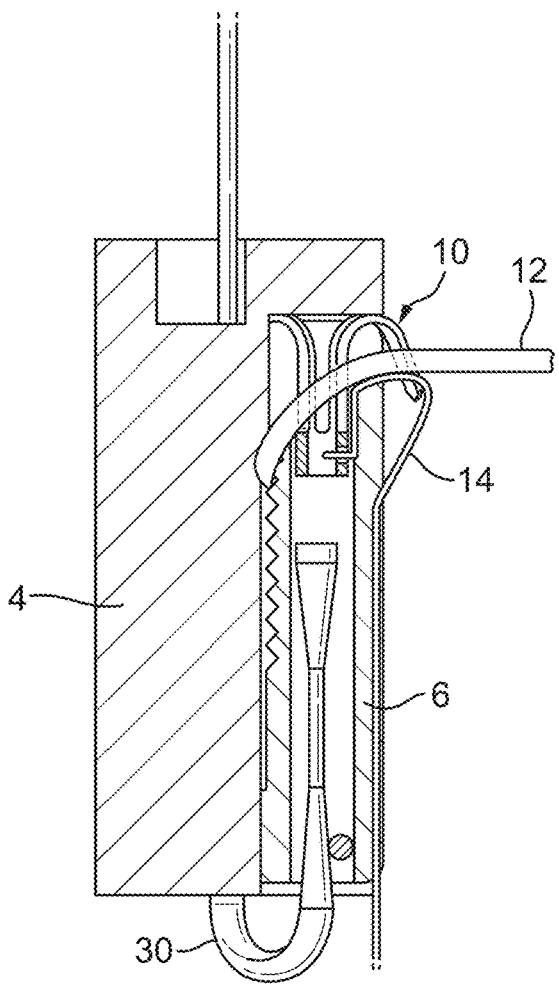
Figure 28:
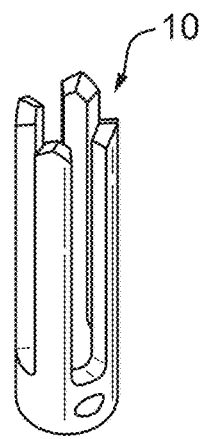
FIGS. 28 and 29 show the leaflet anchor in close-up, in the closed/stowed configuration and in the open/deployed configuration.
Figure 29:
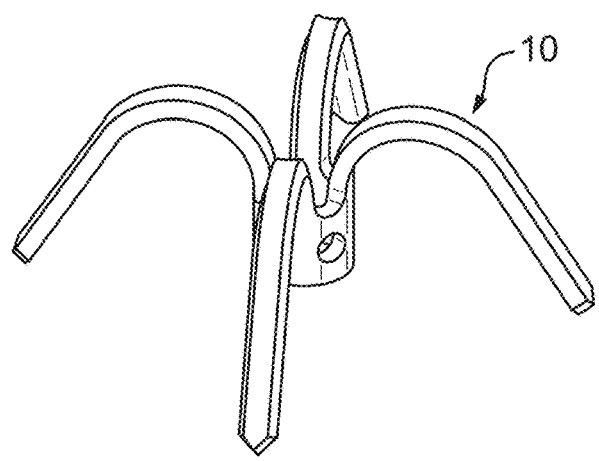

The leaflet anchor 10 is deployed as follows. As shown in FIGS. 23 and 24, the gripper is opened, and then it is closed with the leaflet 12 in position. The nitinol U-rod 30 bends while the gripper is opened and straightens when it is closed. Once the right section of the leaflet 12 is captured then the leaflet anchor 10 is pushed up through the gripper 6 to pierce the leaflet 12 by pulling a wire connected to the nitinol U-rod 30. The U-rod 30 pushes the leaflet anchor 10 when the U-rod wire is pulled. FIG. 25 shows the pierced leaflet 12. The leaflet anchor 10, shown in greater detail in FIGS. 28 and 29, is made of a shape memory material, for example a shape memory metal such as nitinol, to enable it to have an opened out configuration in the form of a set of hooks, whilst also allowing it to be deformed elastically to be stowed within the channel in the gripper arm 6. As noted above, the leaflet fold-out section 24 of the gripper housing 4 allows the leaflet anchor 10 to return to its natural hooked shape. The leaflet 12 in its natural shape is shown in FIG. 26. It is securely fixed to the leaflet 12. The gripper can then release the leaflet 12, as shown in FIGS. 10 and 11, discussed above.

Imaging techniques such as 3-D ultrasound or fluoroscopy can be used when guiding the device and to confirm the correct location of the leaflet 12 within the gripper 6. To assist in this, the echogenic properties of the device may be improved by abrasive blasting, mechanical texture or a special coating. The gripper 6 can also be provided with a detection system to confirm the location of the leaflet 12 within the gripper 6. In a modified gripper (not shown) a fluid based sensor system is provided. This uses holes on the gripping surface of the gripper housing 4. The holes are connected through tubes to a fluid supply, such as contrast fluid from a syringe. When the gripper pinches the leaflet (or other tissue), the holes will be blocked by tissue preventing the flow of fluid. This can be used to determine if the leaflet is in the correct position to deploy the leaflet anchor. The device could be built with various numbers of holes, for example three or four, with the combination of open and closed holes being used to determine the position of the leaflet/tissue within the gripper 4. If four valves are placed in a square pattern, two closed and two open valves, could represent the correct position of the leaflet.

If both anchors 9, 10 have been placed and the position is not ideal, the procedure can be reversed as long as the papillary anchor 9 is in adjustment position. The papillary anchor 9 can be retrieved by pulling it inside the papillary anchor housing 8. The treatment catheter can then be retrieved, leaving the leaflet anchor 10 with the attached wire 14. A retrieval catheter (a tube with slightly larger inner diameter than the leaflet anchor outer diameter) can then be advanced over the wire 14, into the ventricle, and onto the surface of the leaflet 12. When the wire 14 is pulled from the outside, the leaflet anchor 10 folds back into the retrieval catheter. The retrieval catheter is removed and the procedure is back to the starting point.

Figure 27:
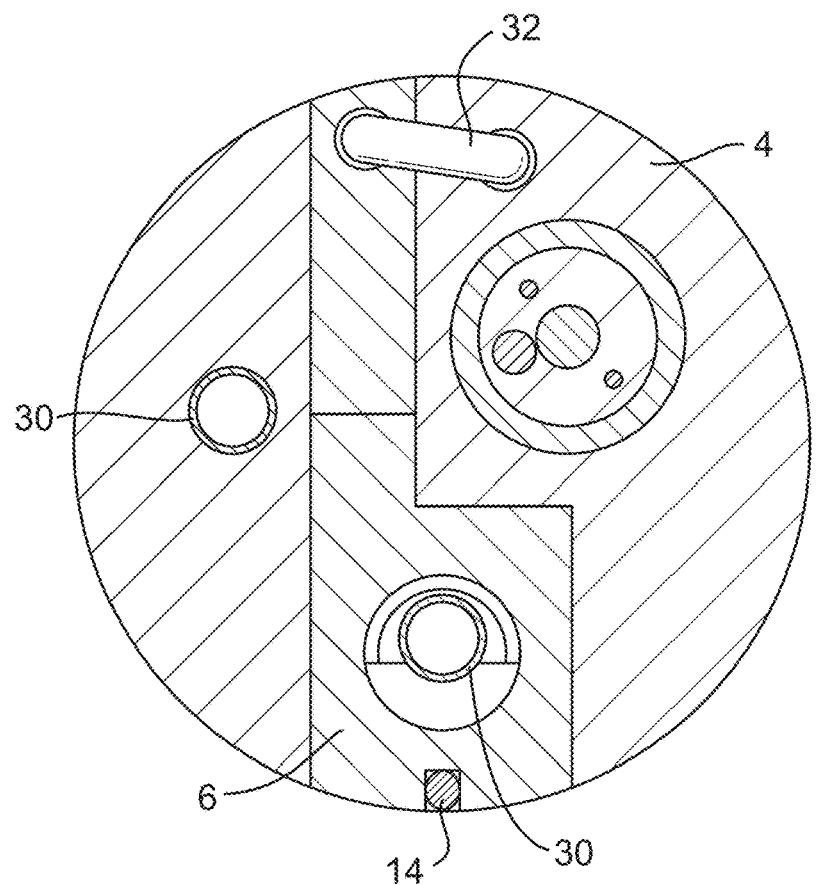
FIG. 27 is a cross-section through a lower part of the catheter device showing how the main parts fit within the treatment catheter.

FIG. 27 is a cross-section through a lower part of the catheter device showing how the main parts fit within the treatment catheter. This illustration shows the cross-section between the papillary anchor housing 8 and the gripper housing 4, looking in an upward direction. The wire 32 that closes the gripper arm 6 goes over a pulley made in the material of the gripper housing 4. The U-rod 30 has a downward part in the main body of the catheter device and an upward part in the gripper arm 6. The cross-section also shows the channel in the gripper for the chord 14, and the main channel of the catheter that holds the safety wire, the chord wire, and a wire connecting to the locking and cutting piece 18.

FIGS. 28 and 29 show the leaflet anchor 10 in close-up, in a closed/stowed configuration (FIG. 28) and in the open/deployed configuration (FIG. 29). The closed configuration is only possible when force is applied to the anchor 10, for example when it is confined within its channel in the gripper 6. When no force is applied then the leaflet anchor 10 returns to the shape shown in FIG. 29, for example when it is pushed out of the channel in the gripper arm 6 and through the leaflet 12.

The leaflet anchor 10 is cut with laser from a nitinol tube and then shape set with heat treatment. After heat treatment it is electropolished to achieve the right properties (the right friction and no sharp edges that could cut the new chord 14).

The chord 14 can be attached to the anchor in several ways. For example, wire through holes with knots or welds. The new chord 14 can be made of Gore-Tex® suture material, or a thin nitinol wire. This preferred embodiment uses Gore-Tex® since it is easier to cut once the length has been adjusted. The new chord 14 has a diameter of approximately 0.1-0.6 mm. The leaflet anchor 10 is approximately 1-2 mm in diameter, and approximately 4-6 mm in length (when straight).

The leaflet anchor pins can be cut with several different profiles to achieve different strength, and/or faster healing. Since the leaflet anchor 10 is cut from tubing using laser cutting then different shapes are easy to produce. The pins of the anchor may for example have a straight edge (minimum friction) or a profile for increased friction, such as a smooth or sharp saw tooth, or a barbed profile. The anchor shape can vary based on the requirements of the procedure. Different anchor designs could be available for a surgeon to select based on their assessment of the patient.

Figure 30:
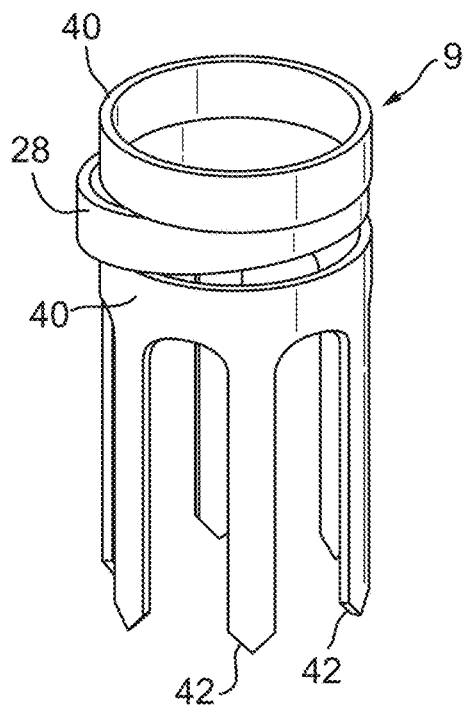
FIGS. 30 to 32 show three configurations for the papillary anchor.
Figure 31:
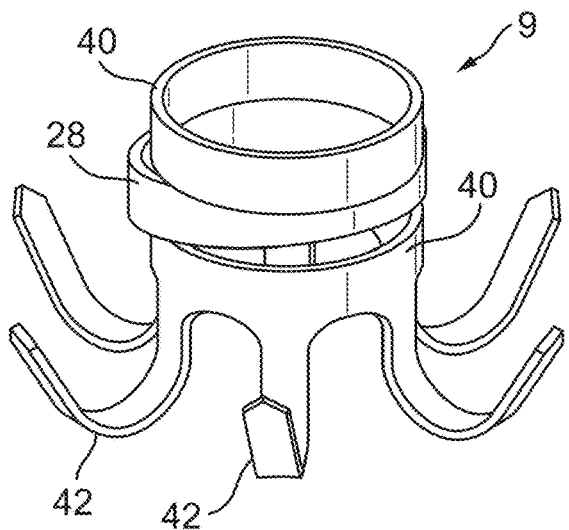
Figure 32:
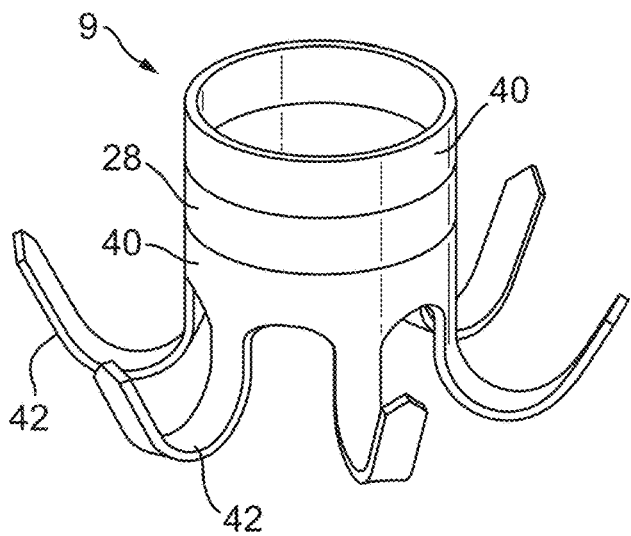

FIGS. 30 to 32 show three configurations for the papillary anchor 9, being the stowed configuration (FIG. 30) when in the papillary anchor housing 8, the adjustment configuration (FIG. 31) where the anchor is placed in the papillary muscle 26 and the chord length can be adjusted (as in FIG. 13), and the locked configuration (FIG. 32) where the chord is locked by the locking segment 28.

The papillary anchor 9 is cut with laser from a nitinol tube, shape set with heat treatment, and electropolished to achieve the right amount of friction to hold the chord without cutting it. The papillary anchor 9 in this example consists of two locking rings 40, one locking segment 28, and six pins 42, which form hooks in the muscle when the anchor is placed. There could of course be a different number of pins, perhaps 3 to 8 pins. The anchor can also be made with multiple locking segments 28 and additional locking rings 40.

The locking segment 28 is a band that is separated from the locking rings 40 by two slits that extend part way around the circumference of the anchor. The slits are sized so that they will grip the chord without cutting it when the locking segment 28 is flush with the locking rings 40. As explained above, the locking and cutting piece 18 is used to hold the locking segment 28 open when it is required to adjust the chord length. The locking is achieved with the internal forces in the nitinol tube as the material will try to return to the un-deformed position (FIG. 32) and pinch the chord once the locking segment 28 is released by the locking and cutting piece 18. The papillary anchor 9 is approximately 4-5 mm in diameter and approximately 10 mm long (when straight).

In an alternative design (not shown) the lower locking ring of the papillary anchor 9 can have a hole that will provide more options in terms of how the chordae is routed through the anchor.

As with the leaflet anchor pins, the papillary anchor pins can be cut with several different shapes to achieve different pull out strength and/or faster healing. The pins of the anchor may for example have a straight edge (minimum friction) or a profile for increased friction, such as a smooth or sharp saw tooth, or a barbed profile. The anchor shape can vary based on the requirements of the procedure. Different anchor designs could be available for a surgeon to select based on their assessment of the patient.

The locking segment 28 on the papillary anchor 9 can be also cut with different structure to achieve optimal locking strength (without cutting the chordae). For example, the edges of the locking segment 28 along the slits (and also the edges of the locking ring along the slits) may be straight, or they may be a saw tooth or wave pattern. The anchor is electro-polished to dull the edges of the locking segment 28 after laser cutting. This ensures that the new chord 14 is not cut by the locking segment 28.

FIGS. 33 to 36 illustrate interaction of the papillary anchor 9 with the chord and a locking and cutting piece 18 of the catheter device. The locking and cutting piece 18, shown in FIG. 33, is made of a suitable biocompatible material, preferably cut with laser and sharpened by grinding away some material to form a V-shaped cutting knife 43. The material may for example be stainless steel, titanium or titanium alloy. Nitinol could also be used. The legs 44 are used to hold the locking segment 28 open to make room for the chord between the locking rings and locking segment 28 in the papillary anchor 9, as shown in FIG. 34. FIG. 35 shows the adjustment catheter 20 in place around the locking and cutting piece 18.

The chord is passed through the cutting and locking piece at least twice, once at the legs 44 for locking and once at the cutting knife 43 for cutting. The chord goes through the catheter, optionally, at a pulley at the side of the housing (as shown in FIG. 36) so that it is held straight when the cutting knife will cut. The locking and cutting piece 18 is approximately 1.5 mm×0.5 mm×15 mm. Note that the pulley could, in a modified design, be stepped in from the side of the housing so that the chord sits in a recess rather than protruding from the housing.

There are various ways to route the chord through the anchor, and these may provide different locking strengths. FIG. 36 shows one option. The chord can be looped around the locking segment 28 once or multiple times, and it can be threaded through a hole in one of the locking rings if this is included, again this can be done once or multiple times.

After the locking has been achieved then the knife 43 will cut the excess chord and the safety wire that goes around the papillary anchor 9 is retracted. It should be noted that the safety wire may pass through a hole in a locking ring 40 or in the locking segment 28, and could be looped around the parts of the papillary anchor in various ways in a similar manner to the chord 14. After the safety wire is retracted then the adjustment catheter 20 is retracted as explained above.

The locking and cutting can be divided into two steps in order to simplify reloading, reduce friction under adjustment and reduce the size of the device. This makes use of a slightly modified arrangement (not shown) where the cutting knife 43 is removed and the cutting piece 18 hence becomes simply a lock pin, with legs 44 as in the Figures but no hole and no cutting edge 43. With this arrangement, both anchors 9, 10 are placed as described above. Once the correct length is achieved, the legs 44 are retracted, which locks the chord 14. The treatment catheter is retracted leaving the excess chord behind. A separate cutting catheter is then advanced over the chord 14, until it reaches the papillary anchor 9, where it can cut the chord 14 to the required length using any suitable mechanism.

One possible design for the cutting catheter (not shown) uses two tubes that slide inside each other, fitting closely together so that a shearing edge can be formed between the tubes. The tubes can each include holes or slots that are aligned to carry the chord 14, and which cut the chord 14 by shearing when they are slid into misalignment. With this arrangement, after the lock pin is removed then the cutting catheter is advanced over the placed chord 14, with the chord 14 through the cutting slots. Once the cutting catheter is in the correct position then a steering wire is pulled in order to move the inner tube. When the edges of the two cutting slots pass each other, the edges works as a scissors and shear the chord 14. The tubes could be arranged with a pulley system, that gives a mechanical advantage to increase the cutting force compared to the force applied to the steering wire. This will allow cutting of a variety of wires such as Nitinol wire, high strength sutures or sutures with a metal core. The inner or outer tube can be made interlocking features to prevent the tubes from rotating relative to one another.

In some cases the natural chordae could be a problem for the device. There is a risk of fouling if one of the existing chordae is caught in the hole provided for the exit of the new artificial chord 14. One way to eliminate this is to have a one way chord exit so that the new chord 14 can only go out of the device, and not in, although this feature is not essential.

Inside the papillary housing 8 there may be small notches in the walls to hold the pins of the papillary anchor 9 and prevent the papillary anchor 9 from rotating so that the pins could fold out in the opening for the new chord 14.

It will be appreciated that the steerable catheter 2 needs a number of lumens. Inside the steerable catheter 2 there will be: U-rod wire, two gripper wires (open and close) and the adjustment catheter 20. Within the adjustment catheter 20 there will be: the safety wire (two parts, as it is a loop), the chord wire (connected to the chordae close to the end of the adjustment catheter 20), and a wire, connected to the locking and cutting piece 18.

Figure 37:
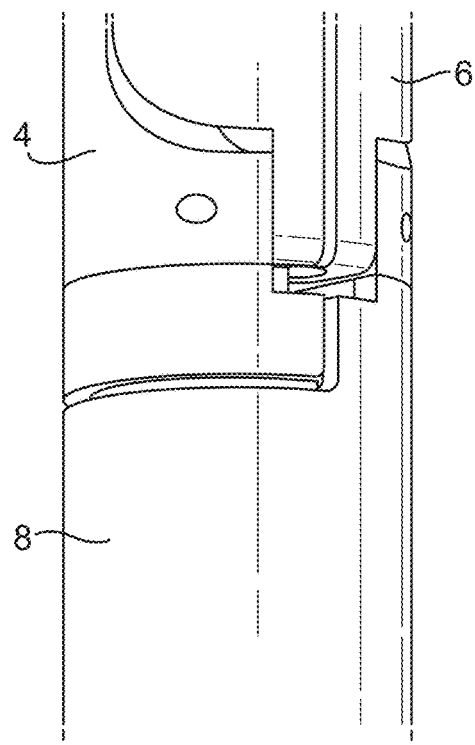
FIG. 37 shows another example arrangement where the chord is routed around the papillary anchor housing.
Figure 38:
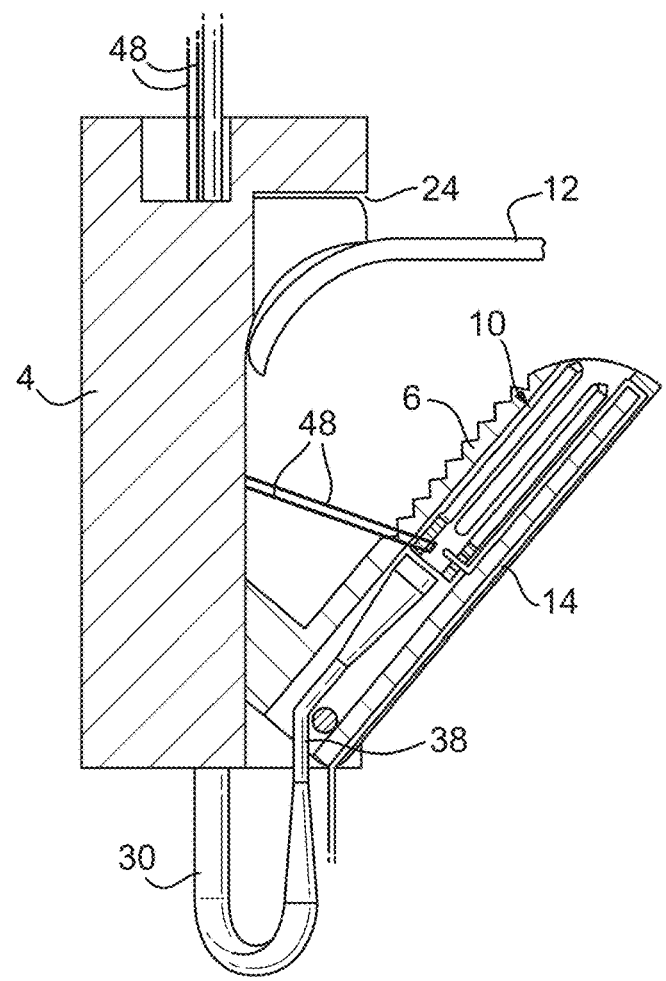
FIGS. 38 to 40 show a slightly modified system using double wires for adjustment of the chord length.
Figure 39:
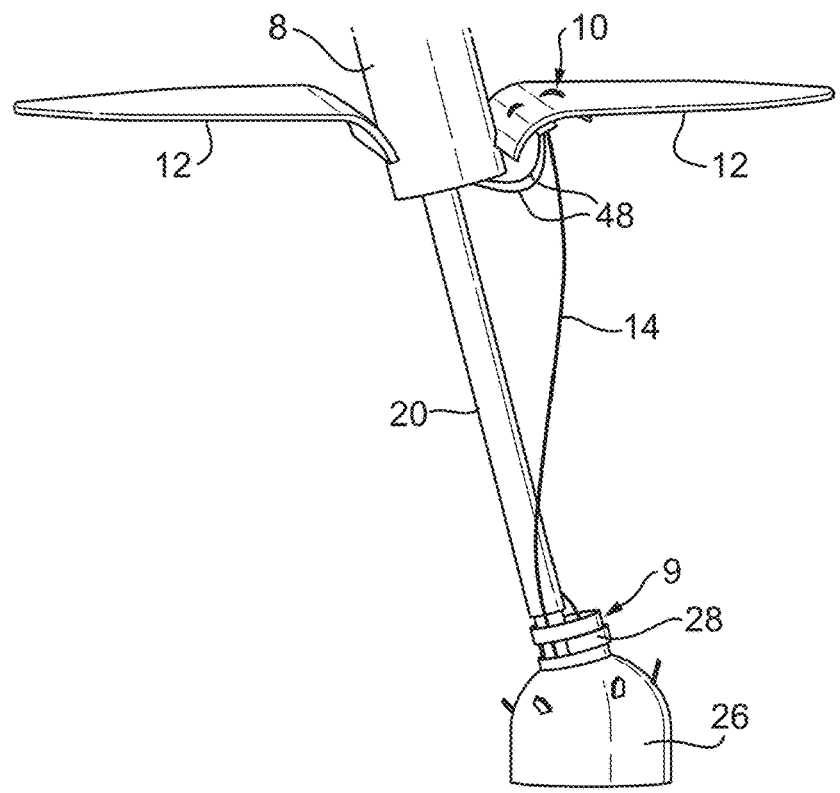

An alternative design of the papillary anchor housing 8 is possible. In the design shown in the earlier drawings the chord channel is straight. This can sometimes generate undesirably high friction. This can be fixed by letting the chord channel go around the papillary anchor housing 8, as shown in FIG. 37. The chord channel will then go from the gripper, to the papillary anchor housing 8, around the papillary anchor housing 8, and then inside the papillary anchor housing 8 (see illustration). The design allows the chordae to go straight into the papillary anchor 9, without getting too much friction from the inside walls of the papillary anchor housing 8.

FIGS. 38 to 41 show a slightly modified system using double wires for adjustment of the chord length. This is an alternative way to adjust the length of the new chord 14. In this design there is a double wire 48 connected to the leaflet anchor 10. The double wire 48 comes out of a passage in the middle of the gripper housing 4 and it passes back along the catheter so that it can be pulled from outside the body.

Figure 40:
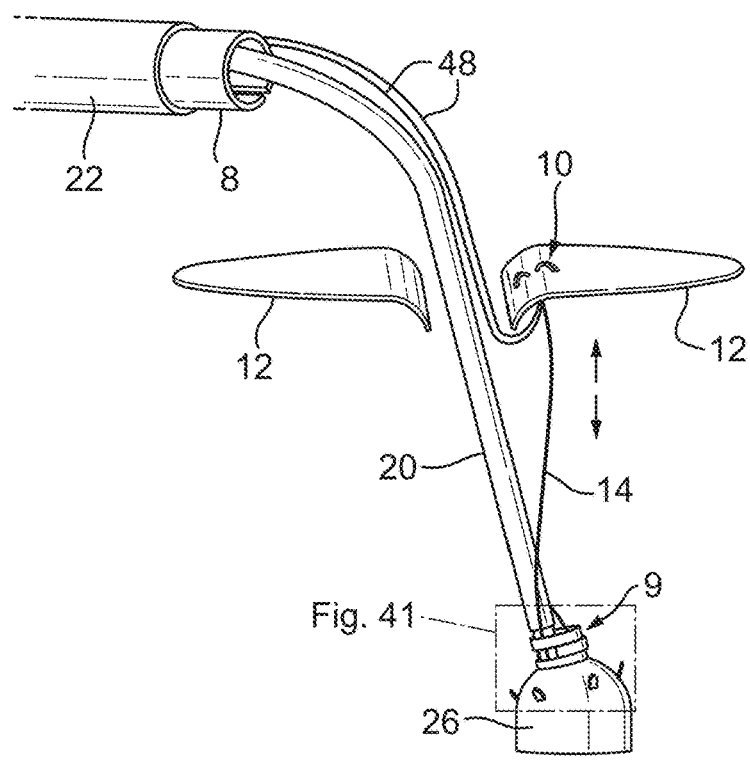

The deployment of the anchors with this design is done the same way as for the system described above, except that when adjusting the chord length it is possible to "pull" the chord longer using the double wire 48 to make it longer, as shown in FIG. 40. The chord can also be pulled to make it shorter by pulling the chord wire, or even by having just a single chord all the way along the catheter to the outside since it only needs to be able to hold tension (as discussed above one reason for the chord wire is so that it can be pushed to lengthen the chord). The double wire can be taken away by pulling one end of the loop out after the procedure is completed.

Figure 41:
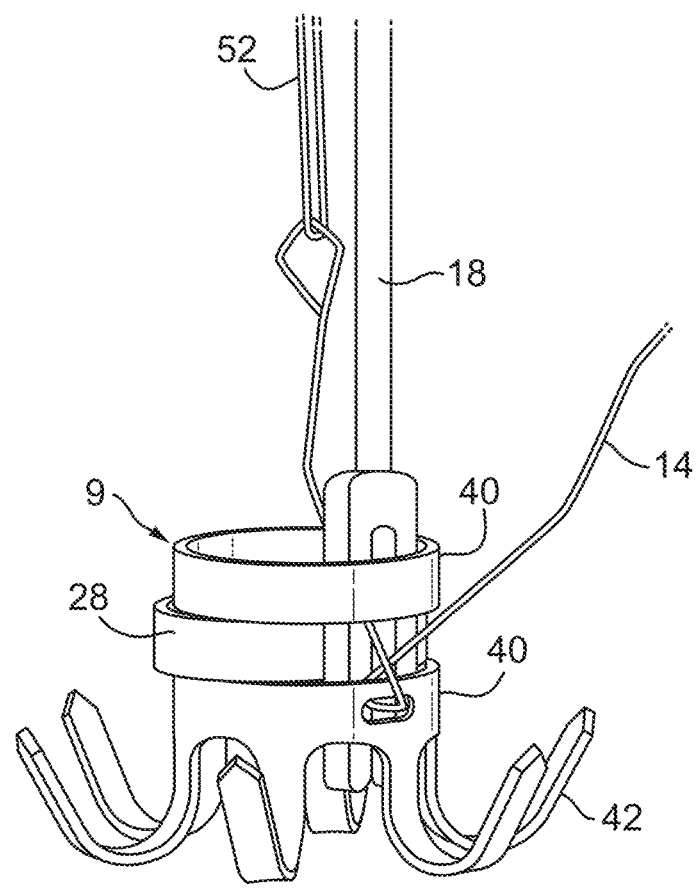
FIG. 41 is a close up of the papillary anchor of FIG. 40 with a slight modification to the double wire system.

Another possibility, as illustrated in FIG. 41, is for the new chord 14 to be pre-cut with a loop to fit a further double wire 52, which can avoid the need for the cutting step. For the sake of clarity the papillary muscle is not shown in FIG. 41. With this arrangement the first double wire (attached to the leaflet anchor 10) can pull on the chord to lengthen it, and the second double wire (attached to the loop) can pull on the chord to shorten it. After the adjustment is completed then the double wire 52 can be removed by pulling one end of the loop.

The catheter system can be built with a snap-fit connection (not shown), that allows the gripper tool tip to be released. This will ease assembly, and could result in a semi-reusable system. In one example the snap-fit connection can be cut (from a tube) with laser in a flexible material, preferable a shape memory alloy such as Nitinol, however, a more rigid material such as stainless steel could also be used. The main body of the catheter and the gripper tool tip fit together in a plug and socket type arrangement, for example with protrusions on one side that fit into recesses on the other side. The protrusions may be deformed elastically while they slide into position and then fit into the recesses. A wider section on the lower part of the connection will prevent movement of the tool tip. This connection could be used on several types of medical instruments, to allow different tool tips or to ease sterilization of the instrument. Small grooves can be provided to allow a tool to lift the protrusion of the snap-fit connection out of the recess to release it. With the use of Nitinol, or a similarly elastic material, then snap-fit joints with geometries of any type commonly used for plastic parts can be used.

Figure 42:
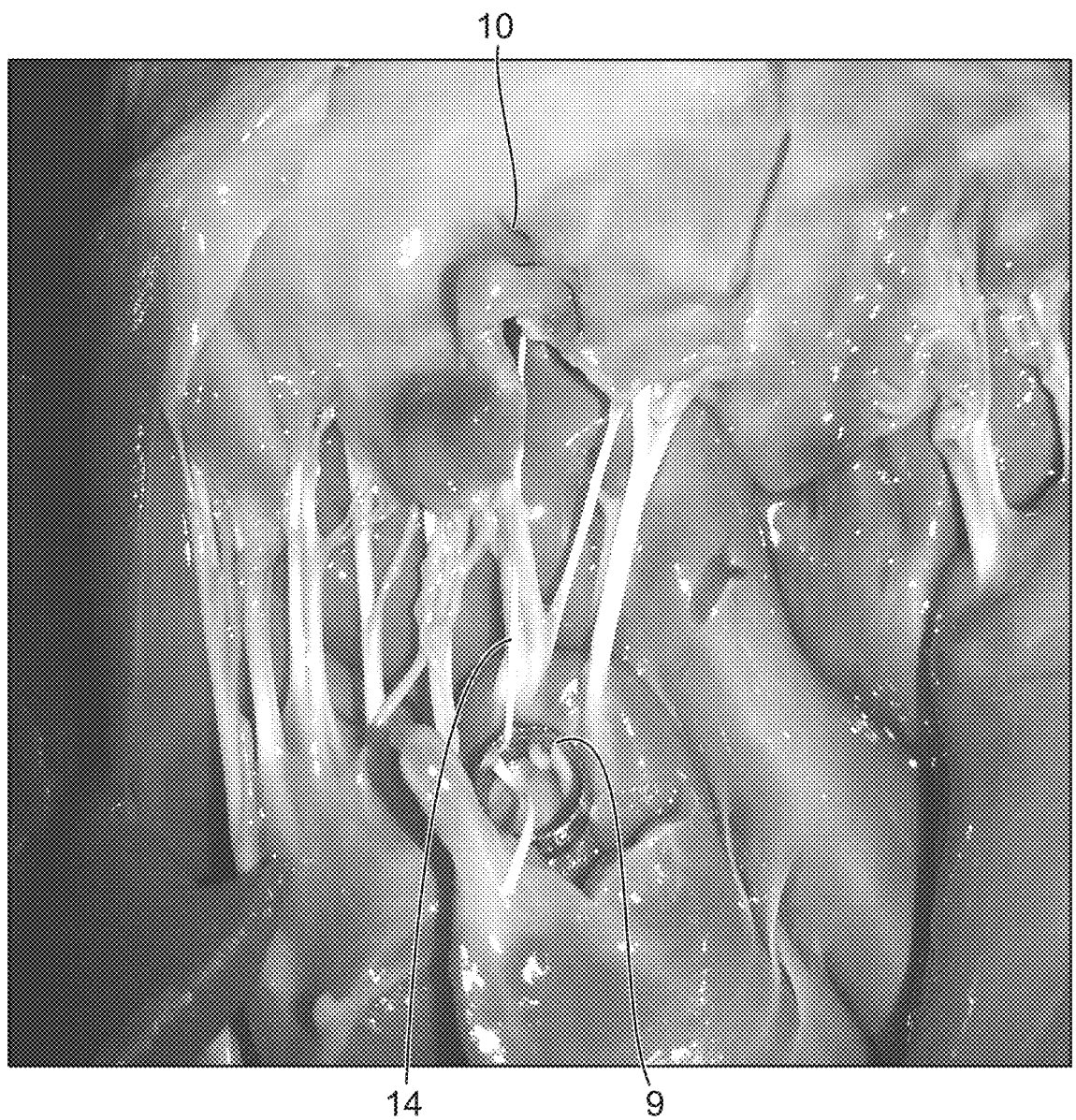
FIG. 42 is a photograph of an inserted papillary anchor and leaflet anchor in a pig's heart.

The procedure of inserting an artificial chord 14 to link the leaflet and papillary muscle has been tested using a pig. FIG. 42 is a photograph of an inserted papillary anchor 9 and leaflet anchor 10 placed inside a dead pig heart, with a new chord 14 passing between the anchors 9, 10. It will be appreciated that this system will provide a way to repair the heart of a human patient in the same way as has been done with the pig in this example.

The device described above could also be used to assist in the implantation of mitral valves. Several interventions to implant mitral-valves through catheters have been tested. The complications related to this procedure are include: aortic obstruction, where the anterior leaflet act as a closing lid which prevents blood flow through the aortic valve; and mitral valve embolism, where the mitral annulus is not a rigid structure and will change over time, valves that are placed with radial pressure are prone to lose their grip and embolism into the atrium.

The proposed device can deal with these problems. The valve can be temporarily placed with radial pressure. Then the catheter device is introduced the same way as described above. Note that the device also could be introduced through the aortic valve for parts of this procedure. The leaflet anchor can be attached to the leaflet and/or through the prosthetic valve. If the only problem is aortic obstruction then the anterior leaflet can be tethered (pulled away from the aortic valve) to the papillary muscles or to the heart wall by a chord fitted by the device. If the need is to anchor a prosthetic valve then the leaflet anchor can be placed in through the frame of the prosthetic valve. Another solution is to attach the leaflet anchor to both the leaflet and the prosthetic valve, and then attach them to the papillary muscle or the heart wall. Multiple anchor pairs can be implanted to ensure that the valve is securely held.

The invention claimed is:

1. An anchor for implantation in body tissue in combination with a line, the anchor comprising:
   a plurality of hooks for engagement with the body tissue, wherein the anchor comprises a folded position and an unfolded position, and is made of an elastic material such that the anchor can be elastically deformed into the folded position by application of a constraining force, and will return to the unfolded position when no constraining force is applied; and
   a locking mechanism for clamping the line when no force is applied, and being elastically deformable to release the line from the locking mechanism for adjustment of a length of the line, wherein the locking mechanism comprises a resiliently deformable locking segment integrated with a wall of the anchor and divided from the wall by at least one slit wherein the resiliently deformable locking segment comprises a band with parallel slits on two sides, such that the band is configured to move out of a plane with the wall to open the parallel slits for adjustment of the length of the line;
   wherein the anchor comprises a tubular body section defining said wall of the anchor;
   wherein said wall includes the resiliently deformable locking segment;
   wherein the plurality of hooks extends from one end of the tubular body section;
   wherein the at least one slit is configured to enable the line to be looped one or more times through the at least one slit; and
   wherein the tubular body section, the resiliently deformable locking mechanism and the plurality of hooks comprise a single, unitary structure comprising the elastic material.

2. An anchor as claimed in claim 1, wherein the anchor is arranged so that when no force is applied, the at least one slit is closed with no gap or a relatively narrow gap in order to clamp the line, whereas when a suitable force is applied to the resiliently deformable locking segment and/or the wall, then the resiliently deformable locking segment and/or the wall will elastically deform to widen an opening provided by the at least one slit so that the line is released.

3. An anchor as claimed in claim 2, the anchor comprising shape memory metal.

4. An anchor as claimed in claim 2, wherein the band can be pulled out of the plane with the wall by application of a force to open the parallel slits.

5. An anchor as claimed in claim 1, wherein the plurality of hooks is formed as sharpened and bent tines at the one end of the tubular body section.

6. An anchor as claimed in claim 1, wherein the anchor comprises a body including the tubular body section defining said wall of the anchor, and the anchor further comprises at least one hole defined through the body for routing the line.

7. An anchor as claimed in claim 1, wherein the anchor is cut from a single tube such that the locking mechanism, the tubular body section and the plurality of hooks are formed of the same tube comprising the elastic material, and wherein the line is looped one or more times through the at least one slit.

8. An anchor as claimed in claim 7, wherein the line comprises a suture material.

9. An anchor as claimed in claim 1, wherein the at least one slit comprises the parallel slits.

10. The anchor as claimed in claim 1, wherein said wall defines the resiliently deformable locking segment.

11. The anchor as claimed in claim 1, wherein the resiliently deformable locking segment constitutes a portion of the wall.

12. The anchor as claimed in claim 1, wherein the wall is a side wall of the tubular body section of the anchor.

13. A method of manufacturing an anchor for implantation in body tissue in combination with a line, the method comprising:
   laser cutting a single tube comprising an elastic material to form the anchor with:
      a plurality of hooks for engagement with the body tissue, wherein the anchor comprises a folded position and an unfolded position, the anchor can be elastically deformed into the folded position by application of a constraining force and the anchor will return to the unfolded position when no constraining force is applied; and
      a locking mechanism for clamping the line when no force is applied, and being elastically deformable to release the line from the locking mechanism for adjustment of a length of the line, wherein the locking mechanism comprises a resiliently deformable locking segment formed in a wall of the anchor and divided from the wall by at least one slit wherein the resiliently deformable locking segment comprises a band with parallel slits on two sides, such that the band is configured to move out of a plane with the wall to open the parallel slits;

wherein the anchor comprises a tubular body section defining said wall of the anchor;

wherein said wall includes the resiliently deformable locking segment;

wherein the plurality of hooks extends from one end of the tubular body section;

wherein the at least one slit is configured to enable the line to be looped one or more times through the at least one slit; and wherein the locking mechanism, tubular body section and plurality of hooks are formed of the same tube comprising the elastic material; and electropolishing the anchor after the laser cutting.

14. A method as claimed in claim 13, wherein laser cutting the tube includes laser cutting the tube to form sharpened tines at one end of the tube, with an other end of the tube forming a body of the anchor and including the wall in which the resiliently deformable locking segment is formed, and further comprising bending the sharpened tines to create the plurality of hooks.

15. A method as claimed in claim 13, wherein the tube comprises a shape memory metal.

16. An anchor for implantation in heart tissue in combination with a line, the anchor comprising:

a tubular body section, the tubular body section including an exterior side wall, the exterior side wall defining a plurality of annular sections;

a deformable locking mechanism configured to clamp the line when no force is applied and to release the line from the deformable locking mechanism for adjustment of a length of the line when force is applied, the deformable locking mechanism comprises a resiliently deformable locking segment of the exterior side wall and is positioned between two locking annular sections of the plurality of annular sections of the exterior side wall; and a plurality of hooks extending from one end of the tubular body section, the plurality of hook configured to engage with body tissue, wherein:

the anchor is configured to be adjusted into a folded position and an unfolded position, and the anchor is configured to transition from the folded position into the unfolded position when no constraining force is applied;

a slit is defined in the exterior side wall while the resiliently deformable locking segment is deformed;

the slit is configured to enable the line to be looped one or more times through the slit; and the tubular body section, the deformable locking mechanism and the plurality of hooks comprise a single, unitary structure comprising an elastic material.

17. The anchor as claimed in claim 16, wherein the plurality of hooks extend from a first locking annular section of the two locking annular sections.

18. The anchor as claimed in claim 16, wherein the anchor is further configured to be adjusted into the folded position, the unfolded position, and a locked position, and wherein, when in the locked position, the resiliently deformable locking segment closes or reduces a size of the slit.

19. The anchor as claimed in claim 16, wherein the anchor is cut from a single tube such that the locking mechanism, the tubular body section and the plurality of hooks are formed of the same tube comprising the elastic material, and wherein the line is looped multiple times.

20. The anchor as claimed in claim 16, wherein the line is looped through the slit to enable both ends the line to move relative to the slit.

* * * * *